United States Patent
Jeanjean et al.

(10) Patent No.: US 11,857,512 B2
(45) Date of Patent: Jan. 2, 2024

(54) PHARMACEUTICAL COMPOSITIONS COMPRISING VENGLUSTAT

(71) Applicant: Genzyme Corporation, Cambridge, MA (US)

(72) Inventors: Audrey Jeanjean, Paris (FR); Danielle Combessis, Paris (FR); David Rigal, Paris (FR); Chris Ho, Bridgewater, NJ (US); Pankaj Taneja, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 17/384,083

(22) Filed: Jul. 23, 2021

(65) Prior Publication Data

US 2022/0023272 A1     Jan. 27, 2022

Related U.S. Application Data

(60) Provisional application No. 63/056,075, filed on Jul. 24, 2020.

(30) Foreign Application Priority Data

Jan. 20, 2021  (EP) .................... 21152595

(51) Int. Cl.
| | |
|---|---|
| A61K 31/439 | (2006.01) |
| A61K 9/00 | (2006.01) |
| A61K 9/20 | (2006.01) |
| A61K 9/48 | (2006.01) |

(52) U.S. Cl.
CPC .......... *A61K 31/439* (2013.01); *A61K 9/0053* (2013.01); *A61K 9/2009* (2013.01); *A61K 9/2013* (2013.01); *A61K 9/2018* (2013.01); *A61K 9/2095* (2013.01); *A61K 9/485* (2013.01); *A61K 9/4833* (2013.01); *A61K 9/4858* (2013.01); *A61K 9/4866* (2013.01)

(58) Field of Classification Search
CPC .. A61K 31/439; A61K 9/0053; A61K 9/2009; A61K 9/2013; A61K 9/2018; A61K 9/2095; A61K 9/4833; A61K 9/485; A61K 9/4858; A61K 9/4866
See application file for complete search history.

(56) References Cited

U.S. PATENT DOCUMENTS

| | | | |
|---|---|---|---|
| 3,119,742 | A | 1/1964 | Heimlich et al. |
| 3,492,397 | A | 1/1970 | David et al. |
| 3,538,214 | A | 11/1970 | Gerald et al. |
| 3,749,787 | A | 7/1973 | Hepworth et al. |
| 4,060,598 | A | 11/1977 | Groppenbacher et al. |
| 4,173,626 | A | 11/1979 | Dempski et al. |
| 4,593,034 | A | 6/1986 | Munson et al. |
| 4,983,600 | A | 1/1991 | Ward et al. |
| 5,025,022 | A | 6/1991 | Naylor et al. |
| 5,106,851 | A | 4/1992 | Turconi et al. |
| 5,236,838 | A | 8/1993 | Rasmussen et al. |
| 5,242,929 | A | 9/1993 | Varasi et al. |
| 5,272,071 | A | 12/1993 | Chappel et al. |
| 5,549,892 | A | 8/1996 | Friedman et al. |
| 5,668,144 | A | 9/1997 | Sabb et al. |
| 5,968,502 | A | 10/1999 | Treco et al. |
| 5,998,429 | A | 12/1999 | Macor et al. |
| 6,066,626 | A | 5/2000 | Yew et al. |
| 6,124,354 | A | 9/2000 | Akerblom et al. |
| 6,468,998 | B1 | 10/2002 | Kuroita |
| 6,492,386 | B2 | 12/2002 | Myers et al. |
| 6,599,916 | B2 | 7/2003 | Myers et al. |
| 6,780,861 | B2 | 8/2004 | Nozulak |
| 6,916,828 | B2 | 7/2005 | Farreons et al. |
| 6,953,855 | B2 | 10/2005 | Mazurov et al. |
| 6,987,106 | B1 | 1/2006 | Gallet et al. |
| 7,115,629 | B2 | 10/2006 | Farrerons Gallemi et al. |
| 7,138,410 | B2 | 11/2006 | Luithe et al. |
| 7,273,872 | B2 | 9/2007 | Tracey et al. |
| 7,332,524 | B2 | 2/2008 | Linders et al. |
| 7,435,742 | B2 | 10/2008 | Prat Quinones et al. |
| 7,776,879 | B2 | 8/2010 | Buil Albero et al. |
| 7,985,760 | B2 | 7/2011 | Ali et al. |
| 8,003,617 | B2 | 8/2011 | Cheng et al. |
| 8,039,483 | B2 | 10/2011 | Amari et al. |
| 8,252,789 | B2 | 8/2012 | Lingwood et al. |

(Continued)

FOREIGN PATENT DOCUMENTS

| | | |
|---|---|---|
| CA | 2066696 | 3/1991 |
| CA | 2182568 | 8/1995 |

(Continued)

OTHER PUBLICATIONS

Aerts, et al., "Elevated Globotriaosylsphingosine is a Hallmark of Fabry Disease," PNAS USA, 105: 2812-2817 (2008).

Alam, et al., "Glucosylceramide synthase inhibitors differentially affect expression of glycosphingolipds," Glycobiology, 25(4): 351-356 (2015).

Banker, et al., "Prodrugs," Modern Pharmaceutics, pp. 451 and 596.

Barton, et al., "Replacement Therapy for Inherited Enzyme Deficiency—Macrophage-targeted Glucocerebrosidase for Gaucher's Disease," New England Journal of Medicine, 324: 1464-1470 (1991).

Beniaminovitz, et al., "Prevention of Rejection in Cardiac Transplantation by Blockade of the Interleukin-2 Receptor with a Monoclonal Antibody," New England Journal of Medicine, 342: 613-619 (2000).

(Continued)

*Primary Examiner* — Robert A Wax
*Assistant Examiner* — Olga V. Tcherkasskaya
(74) *Attorney, Agent, or Firm* — Hoxie & Associates LLC

(57) ABSTRACT

The present disclosure relates to pharmaceutical compositions, including dosage forms, such as tablets or capsules, comprising venglustat, in free base, or pharmaceutically acceptable salt form, a diluent/filler and a lubricant, optionally in combination with one or more additional therapeutic agents, to processes for manufacture thereof, and to methods of use in the treatment or prevention of disease.

12 Claims, 1 Drawing Sheet

(56) References Cited

U.S. PATENT DOCUMENTS

| | | |
|---|---|---|
| 8,349,319 B2 | 1/2013 | Schuchman et al. |
| 8,367,696 B2 | 2/2013 | Nagashima et al. |
| 8,389,517 B2 | 3/2013 | Ibraghimov et al. |
| 8,791,123 B2 | 7/2014 | Allen et al. |
| 8,993,556 B2 | 3/2015 | Brasca et al. |
| 9,108,975 B2 | 8/2015 | Tamura et al. |
| 9,126,993 B2 | 9/2015 | Bourque et al. |
| 9,139,580 B2 | 9/2015 | Bourque et al. |
| 9,440,976 B2 | 9/2016 | Dyke et al. |
| 9,518,049 B2 | 12/2016 | Siegel et al. |
| 9,655,946 B2 | 5/2017 | Alexiou et al. |
| 9,682,975 B2 | 6/2017 | Siegel et al. |
| 9,845,327 B2 | 12/2017 | Krainc et al. |
| 10,065,949 B2 | 9/2018 | Siegel et al. |
| 10,604,518 B2 | 3/2020 | Siegel et al. |
| 10,954,230 B2 | 3/2021 | Siegel et al. |
| 11,008,316 B2 | 5/2021 | Bourque et al. |
| 2002/0177591 A1 | 11/2002 | O'Donnell et al. |
| 2004/0002513 A1 | 1/2004 | Mazurov et al. |
| 2005/0031683 A1* | 2/2005 | Kapoor .......... A61K 31/47 424/464 |
| 2005/0239774 A1 | 10/2005 | Ernst et al. |
| 2006/0058349 A1 | 3/2006 | Ali et al. |
| 2007/0213350 A1 | 9/2007 | Tracey et al. |
| 2007/0249588 A1 | 10/2007 | Ernst et al. |
| 2008/0234324 A1 | 9/2008 | Orchard et al. |
| 2009/0131470 A1 | 5/2009 | Walmsley et al. |
| 2009/0163500 A1 | 6/2009 | Lingwood et al. |
| 2009/0017847 A1 | 7/2009 | Lee et al. |
| 2009/0318491 A1 | 12/2009 | Picciotto et al. |
| 2010/0113517 A1 | 5/2010 | Palling |
| 2010/0190761 A1 | 7/2010 | Ogawa et al. |
| 2011/0052559 A1 | 3/2011 | Schuchman et al. |
| 2012/0157464 A1 | 6/2012 | Feurbach et al. |
| 2014/0228575 A1 | 8/2014 | Bellunt et al. |
| 2014/0255381 A1 | 9/2014 | Bourque et al. |
| 2014/0371460 A1 | 12/2014 | Bourque et al. |
| 2015/0210681 A1 | 7/2015 | Bourque et al. |
| 2016/0039805 A1* | 2/2016 | Siegel .......... A61P 25/00 546/137 |
| 2016/0039806 A1 | 2/2016 | Siegel et al. |
| 2016/0207933 A1 | 7/2016 | Bourque et al. |
| 2016/0361301 A1* | 12/2016 | Leonard .......... A61P 9/00 |
| 2017/0334903 A1 | 11/2017 | Siegel et al. |
| 2018/0036295 A1 | 2/2018 | Cheng et al. |
| 2018/0065957 A1 | 3/2018 | Bourque et al. |
| 2019/0031652 A1 | 1/2019 | Siegel et al. |
| 2020/0048266 A1 | 2/2020 | Bourque et al. |
| 2020/0181137 A1 | 6/2020 | Siegel et al. |
| 2020/0222310 A1* | 7/2020 | Purohit .......... A61K 47/10 |
| 2021/0251982 A1 | 8/2021 | Crawford et al. |
| 2021/0261557 A1 | 8/2021 | Bourque et al. |
| 2022/0016092 A1 | 1/2022 | Crawford et al. |
| 2022/0110922 A1 | 4/2022 | Ibraghimov-Beskrovnaya et al. |

FOREIGN PATENT DOCUMENTS

| | | |
|---|---|---|
| CA | 2398754 | 8/2001 |
| DE | 1768808 | 1/1972 |
| DE | 1326510 | 2/1995 |
| EP | 0 747 355 | 12/1996 |
| EP | 1300407 | 4/2003 |
| GB | 725228 | 3/1995 |
| JP | H-08198751 | 8/1996 |
| JP | 2002302490 | 10/2002 |
| JP | 2003267977 | 9/2003 |
| WO | WO 1995/021820 | 8/1995 |
| WO | WO 1997/017348 | 5/1997 |
| WO | WO 1998/004517 | 2/1998 |
| WO | WO 2000/026186 | 5/2000 |
| WO | WO 2000/058311 | 10/2000 |
| WO | WO 2001/085727 | 11/2001 |
| WO | WO 2002/015662 | 2/2002 |
| WO | WO 2002/016356 | 2/2002 |
| WO | WO 2003/078431 | 9/2003 |
| WO | WO 2004/000840 | 12/2003 |
| WO | WO 2004/007453 | 1/2004 |
| WO | WO 2004/016617 | 2/2004 |
| WO | WO 2004/011430 | 5/2004 |
| WO | WO 2004/052365 | 6/2004 |
| WO | WO 2004/056745 | 7/2004 |
| WO | WO 2005/061510 | 7/2005 |
| WO | WO 2005/068426 | 7/2005 |
| WO | WO 2005/073183 | 8/2005 |
| WO | WO 2006/002375 | 1/2006 |
| WO | WO 2006/134318 | 12/2006 |
| WO | WO 2007/038367 | 4/2007 |
| WO | WO 2007/083978 | 7/2007 |
| WO | WO 2007/100430 | 9/2007 |
| WO | WO 2008/156721 | 12/2008 |
| WO | WO 2010/014455 | 2/2010 |
| WO | WO 2010/015324 | 2/2010 |
| WO | WO 2010/091104 | 8/2010 |
| WO | WO 2010/091164 | 8/2010 |
| WO | WO 2010/121963 | 10/2010 |
| WO | WO 2011/006074 | 1/2011 |
| WO | WO 2011/009890 | 1/2011 |
| WO | WO 2011/073263 | 6/2011 |
| WO | WO-2011141483 A2 * | 11/2011 ......... A61K 31/4545 |
| WO | WO 2012/129084 | 9/2012 |
| WO | WO 2012/177997 | 12/2012 |
| WO | WO 2014/041425 | 3/2014 |
| WO | WO-2016145046 A1 * | 9/2016 ............. A61K 31/00 |
| WO | WO-2021061701 A1 * | 4/2021 ............. A61P 43/00 |

OTHER PUBLICATIONS

Brenkert, et al., "Synthesis of Galactosyl Ceramide and Glucosyl Ceramide by Rat Brain: Assay Procedures and Changes with Age," Brain Research, 36: 183-193 (1971).

Cabrera-Salazar, et al., "Intracerebroventricular Delivery of Glucocerebrosidase Reduces Substrates and Increases Lifespan in a Mouse Model of Neuronopathic Gaucher Disease," Experimental Neurology, 225: 436-444 (2010).

Chirmule, et al., "Readministration of Adenovirus Vector in Non-human Primate Lungs by Blockade of CD40-CD40 Ligand Interactions," J. Virol., 74: 3345-3352 (2000).

Conradi, et al., "Late-infantile Gaucher Disease in a Child with Myoclonus and Bulbar Signs: Neuropathological and Neurochemical Findings," Acta Neuropathologica, 82: 152-157 (1991).

Czartoryska, et al., "Changes in Serum Chitotriosidase Activity with Cessation of Replacement Enzyme (Cerebrosidase) Administration in Gaucher Disease," Clin. Biochem., 33: 147-149 (2000).

Czartoryska, et al., "Serum Chitotriosidase Activity in Gaucher Patients on Enzyme Replacement Therapy (ERT)," Clin. Biochem., 31: 417-420 (1998).

Den Tandt, et al., "Marked Increase of Methylumbelliferyl-tetra-N-acetylchitotetraoside Hydrolase Activity in Plasma from Gaucher Disease Patients," J. Inherit. Metab. Dis., 19: 344-350 (1996).

El Alwani, et al., "Regulation of the Sphingolipidsignaling Pathways in the Growing and Hypoxic Rat Heart," Prostaglandins & Other Lipid Mediators, 78(1-4): 249-263 (2005).

Enquist, et al., "Murine Models of Acute Neuronopathic Gaucher Disease," PNAS, 104: 17483-17488 (2007).

European Search Report for EP 2685986, "Glucosylceramide Synthase Inhibitors," dated Feb. 4, 2015.

Fishwild, et al., "Differential Effects of Administration of a Human Anti-CD4 Monoclonal Antibody, HM6G, in Nonhuman Primates," Clin. Immunol., 92: 138-152 (1999).

Gaziev, et al., "Chronic graft-versus-host disease: is there an alternative to the conventional treatment?" Bone Marrow Transplant, 25: 689-696 (2000).

Giri, et al., "Krabbe Disease: Psychosine-mediated Activation of Phospholipase A2 in Oligodendrocyte Cell Death," Journal of Lipid Research, 47: 1478-1492 (2006).

Gummert, et al., "Newer Immunosuppressive Drugs: A Review," J. Am. Soc. Nephrol., 10: 1366-1380 (1999).

Gura, Trisha, "Systems for identifying new drugs are often faulty," Science 7, 278(5340): 1041-1042 (1997).

(56) References Cited

OTHER PUBLICATIONS

Guo, et al., "Elevated Plasma Chiotriosidase Activity in Various Lysosomal Storage Disorders," J. Inherit. Metab. Dis., 18: 717-722 (1995).
Hollak, et al., "Marked Elevation of Plasma Chitotriosidase Activity: A Novel Hallmark of Gaucher Disease," J. Clin. Invest., 93: 1288-1292 (1994).
Ida, et al., "Clinical and Genetic Studies of Japanese Homozygotes for the Gaucher Disease L444P Mutation," Human Genetics, 105: 120-126 (1999).
International Search Report for WO 2012/0129084, dated Jul. 2, 2013.
Ito, et al., "Induction of CTL Responses by Simultaneous Administration of Liposomal Peptide Vaccine with Anti-CD40 and Anti-CTLA-4 mAb," J. Immunol., 164: 1230-1235 (2000).
Johnson, et al., "Relationship between drug activity in NCI preclinical in vitro and in vivo models and early clinical trials," British Journal of Cancer, 84(10): 1424-1431 (2001).
Leonard, et al., "Cytokine receptor signaling pathways," J. Allergy Clin. Immunol., 105: 877-888 (2000).
Liu, et al., "Mice with type 2 and 3 Gaucher Disease Point Mutations Generated by a Single Insertion Mutagenesis Procedure (SIMP)," PNAS, 95: 2503-2508 (1998).
Marinova-Mutafchieva, et al., "A Comparative Study into the Mechanisms of Action and Anti-Tumor Necrosis Factor a/Anti-CD4, and Combined Anti-Tumor Necrosis Factor a/Anti-CD4 Treatment in Early Collagen-Induced Arthritis," Arthritis Rheum., 43: 638-644 (2000).
Marks, et al., "Identification of Active Site Residues in Glucosylceramide Synthase," Journal of Biological Chemistry, 276: 26492-26498 (2001).
Marshall, et al., "Substrate Reduction Augments the Efficacy of Enzyme Therapy in a Mouse Model of the Fabry Disease," PLoS One, 53: 15033 (2010).
Natoli Ta., "Inhibition of glucosylceramide accumulation results in effective blockade of polycystic kidney disease in mouse models," Nat Med., 16(7): 788-792 (2010).
Nevins, "Overview of new immunosuppressive therapies," Curr. Opin. Pediatr., 12: 146-150 (2000).
O'Donnell, C.J., et al., "Synthesis and SAR Studies of 1,4-diazibicyclo[3.2.2]nonane phenyl carbamates—Subtype Selective, High Affinity α7 Nicotinic Acetylcholine Receptor Agonists," Bioorganic and Medicinal Chemistry Letters, 19: 4747-4751 (2009).
Orvisky, et al., "Glucosylsphingosine Accumulation in Mice and Patients with Type 2 Gaucher Disease Begins Early in Gestation," Pediatric Research, 48: 233-237 (2000).
Pastores, et al., "Enzyme Therapy in Gaucher Disease Type 1: Dosage Efficacy and Adverse Effects in 33 Patients Treated for 6 to 24 Months," Blood, 82: 408-416 (1993).
Przepiorka, et al., "A Phase II Study of BTI-322, a Monoclonal Anti-CD2 Antibody, for Treatment of Steroid-Resistant Acute Graft-Versus-Host Disease," Blood, 92: 4066-4071 (1998).
Qi, et al., "Effect of Tacrolimus (FK506) and Sirolimus (Rapamycin) Mono- and Combination Therapy in Prolongation of Renal Allograft Survival in the Monkey," Transplantation, 69: 1275-1283 (2000).
Shapiro, et al., "Islet Transplantation in Seven Patients with Type 1 Diabetes Mellitus Using a Glucocorticoid-Free Immunosuppressive Regimen," New England Journal of Medicine, 343: 230-238 (2000).
Shayman, JA., "Targeting Glucosylceramide Synthesis in the Treatment of Rare and Common Renal Disease," Semin Nephrol., 38(2):183-192, (2018).
Sun, et al., "Neuronopathic Gaucher Disease in the Mouse Viable Combined Selective Saposin C Deficiency and Mutant Glucocerebrosidase (V394L) Mice with Glucosylsphingosine and Glucosylceramide Accumulation and Progressive Neurological Deficits," Hum. Mol. Genet., 19: 1088-1097 (2010).
Turzanski, et al., "P-Glycoprotein is Implicated in the Inhibition of Ceramide-induced Apoptosis in TF-1 Acute Myeloid Leukemia Cells by Modulation of the Glucosylceramide Synthase Pathway," Experimental Hematology, 33(1): 62-72 (2005).
Wolff, et al., "Some consideration for prodrug design," Burger's Medicinal Chemistry and Drug Discovery, Fifth Edition, 1: 975-977 (1995).
Wong, Manfred E., "Neuropathology Provides Clues to the Pathophysiology of Gaucher Disease," Molecular Genetics and Metabolism, 82: 192-207 (2004).
Yamashita, et al., "A vital role for glycosphingolipid synthesis during development and differentiation," Proc. Natl. Acad. Sci., 99(16): 9142-9147 (1999).
Auray-Blais C., et al., "How Well Does Urinary Lyso-gb3 Function as a Biomarker in Fabry Disease?," Clinica Chimica Acta, 2010, vol. 411 (23-24), pp. 1906-1914.
Bangari, et al., "Progressive Organ Pathology Resembles the Type 2 Later-Onset Phenotype of Fabry Disease," The American Journal of Pathology, 185 (3):651-665 (2015).
Bastin R.J., et al., "Salt Selection and Optimisation for Pharmaceutical New Chemical Entities," Organic Process Research & Development, 2000, vol. 4 (5), pp. 427-435.
Branco L., et al., "Selective Deletion of Antigen-Specific, Activated T Cells by a Humanized MAB to CO2 {Medi-507) s Mediated by NK Cells," Transplantation, 1999, vol. 68 (10), pp. 1588-1596.
Brat, et al., "Tau-associated Neuropathology in ganglion cell tumours increases with patient age but appears unrelated to ApoE genotype," Neuropathology and Applied Neurobiology, vol. 27 (2001), pp. 197-205.
Bremova-Ertl, et al., "Oculomotor and Vestibular Findings in gaucher Disease Type 3 and Their correlation with neurological Findings" Frontiers in Neurology 2018, vol. 8, pp. 1-19.
Bundgard, Design of Prodrugs, pp. 7-9, 21-24 (1985).
CAS Registration No. 865147-82-6.
CAS Registration No. 1070460-12-6.
Caira M.R., "Crystalline Polymorphism of Organic Compounds," Topics in Current Chemistry, 1999, vol. 198, pp. 163-208.
Demain et al., Enantiomeric purity determination of 3-aminoquinuclidine by diastereomeric derivatization and high-performance liquid chromatographic separation, Journal of Chromatography, vol. 466: 415-420 (1989).
Feuerbach, et al., "JN403, in vitro characterization of a novel nicotinic acetylcholine receptor α7 selective agonist" Neuroscience Letters, 2007, vol. 416, pp. 61-65.
Gaenslen, A., et al., "The Patient's Perception of Prodromal Symptoms Before the Initial Diagnosis of Parkinson's Disease," Movement Disorders: Official Journal of Movement Disorder Society, 26(4): 653-658, 656 (2011).
Gambarin, F., et al., "When Should Cardiologists Suspect Anderson-Fabry Disease?" The American Journal of Cardiology, 106(10): 1492-1499 (2010).
Goedert, "Tau Gene Mutations and Their Effects," Movement Disorders, vol. 20 (2005),pp. S45-S52.
Gundisch, et al., "Synthesis and Evaluation of phenylcarbamate derivatives as lignads for nicotinic acetylcholine receptors," Bioorganic & Medicinal Chemistry, 2004, vol. 12, pp. 4953-4962.
Hollak, et al., (Expert Opinion Ther. Targets (2007) 11:821-833). (Year: 2007).
Horak et al., Optimization of a ligand immobilization and azide group endcapping concept via "Click-Chemistry" for the preparation of adsorbents for antibody purification, Journal of Chromatography B, Analytical Technologies in the Biomedical and Life Science, 2010, vol. 878(32): 3382-3394.
Irvine et al. (Mol Med. Jul.-Aug. 2008; 14(7-8): 451-464).
Jordan, V. C. Nature Reviews: Drug Discovery, 2, 2003, pp. 205-213.
JP2002302490, Pfizer Products, Inc., "Medicinal Composition for Treating CNS Disorder and Other Disorder," Oct. 18, 2002, English language machine translation of abstract, Espacenet, date obtained: Apr. 5, 2019, 2 pages.
Kloe, G., et al., "Surface Plasmon Resonance Biosensor Based Fragment Screening Using Acetylcholine Binding Protein Identifies Ligand Efficiency Hot Spots (LE Hot Spots) by Deconstruction of Nicotinic Acetylcholine Receptor a7 Ligands," Journal of Medicinal Chemistry, 53: 7192-7201 (2010).
Kodanko J.J., et al., "Synthesis of Diethynyltriptycene-linked Dipyridyl Ligands," Organic Letters, 2005, vol. 7 (21), pp. 4585-4588.

(56) References Cited

OTHER PUBLICATIONS

Kurlberg G., et al., "Blockade of the B7-CD28 Pathway by CTLA4-1g Counteracts Rejection and Prolongs Survival n Small Bowel Transplantation," Scandinavian Journal of Immunology, 2000, vol. 51 (3), pp. 224-230.
Lee, V., "Mechanisms of Parkinson's Disease Linked to Pathological α-Synuclein: New Targets for Drug Discovery," Elsevier Inc., Neuron 52:33-38 (2006).
Marshall, J., et al., "CNS-accessible Inhibitor of Glucosylceramide Synthase for Substrate Reduction Therapy of Neuronpathic Gaucher Disease," Official Journal of the American Society of Gene & Cell Therapy, 2016, vol. 24(6), DD. 1019-1029.
Mashkovsky, The Relationship Between the Chemical Structure and Pharmacological Activity of Some Esters of3-Hydroxyquinuclidine (Quinuclidine-3-0L}, Proc. Intern. Pharrnacol. Meeting, 1st, Stockholm, 1961, 1963, vol. 7: 356-366.
Masjedizadeh, et al., "Synthesis of Tritum Labelled (R) and (S)-3Aminoquinuclidine: A Ubiquitous Componet of Serotin Receptor Ligands, Part I" Journal of Labelled Compunds and Radiopharmaceuticals, 1996, vol. 38, pp. 40-51.
Merrill et al., Sphingolipidomics: High-throughput, structure-speciWc, and quantitative analysis of sphingolipids by liquid chromatographytandem mass spectrometry, Methods 36: 207-224 (2005).
Naito, R., et al., "Selective Muscarinic Antagonists. II.(1) Synthesis and Antimuscarinic Properties of Biphenylylcarbamate Derivatives," Chem. Pharm. Bull., 1998, vol. 46(8), pp. 1286-1294.
Nilsson 0., et al., "Accumulation of Glucosylceramide and Glucosylsphingosine (Psychosine) in Cerebrum and Cerebellum in Infantile and Juvenile Gaucher Disease," Journal of Neurochemistry, 1982, vol. 39 (3), pp. 709-718.
Noelker, C., et al., "Glucocerebrosidase deficiency and mitochondrial impairment in experimental Parkinson disease," Journal of the Neurological Sciences, Elsevier, 356(1-2): 129-136 (2015).
Orr, et al., "A Brief Overview of Tauopathy: Causes, Consequences, and Therapeutic Strategies," Trends Pharmacol Sci. (2017) 38(7): pp. 637-648. doi: 10.1016/i .tips.2017 .03 .011.
Palavra, et al., (Neurology Research International (2013) p. 1-8, ID:576091).
Ross, C. & Poirier, M., "Protein aggregation and neurodegenerative disease," Nature Medicine 10, S10-S17, Abstract (2004).
Ryan E.A., et al., "Clinical Outcomes and Insulin Secretion after Islet Transplantation with the Edmonton Protocol,"Diabetes, 2001, vol. 50 (4), pp. 710-719.
Sardi, S.P., et al., "Glucosylceramide synthase inhibition reduces a-synuclein pathology and improves cognition in murine models of synucleinopathy," Molecular Genetics and Metabolism, 117(2): S102. (Abstract Only).
Scholl, M., et al., "In Vivo Braak Staging Using 18F-AV1451 Tau PET Imaging," Alzheimer's & Dementia 11(7): Suppl. P4 (Jul. 2015).
Shen, W., et al., "Inhibition of glucosylceramide synthase stimulates autophagy flux in neurons," Journal of Neurochemistry, 129: 884-894 (2014).
Skorvanek M et al., *Mov Disord Clin Pract* 2017; 4: 536-544.
"Tauopathy," Standardofcare.com, https://standardofcare.com/tauopathy/ (2022).
Thurberg, B., et al., "Monitoring the 3-Year Efficacy of Enzyme Replacement Therapy in Fabry Disease by Repeated Skin Biopsies" The Journal of Investigative Dermatology, 2004, vol. 122, pp. 900-908.
Thurberg, et al., "Cardiac Microvascular Pathology in Fabry Disease Evaluation of Endomyocardial Biopsies Before and After Enzyme Replacement Therapy," Circulation, 119(19):2561-2567 (2009).
Urbanelli, L., et al., "Therapeutic Approaches for Lysosomal Storage Diseases: A Patent Update," Recent Patents on CNS Drug Discovery, 8(2): 1-19 (2013).
Wiersma, et al., "Untangling the origin and function of granulovacuolar degeneration bodies in neurodegenerative proteinopathies," Acta Neuropathologica Communications vol. 8 (2020) pp. 153.
Wemheuer, W., et al., "Types and Strains: Their Essential Role in Understanding Protein Aggregation in Neurodegenerative Diseases," Frontiers in Aging Neuroscience, 9: 187 (2017).
WO1995021820, Yamanouchi Pharma Co. Ltd., "Novel Carbamate Derivative and Medicinal Composition Containing the Same," Aug. 17, 1995, English language machine translation of abstract, Espacenet, date obtained: Apr. 5, 2019, 2 pages.
WO2000026186, Yoshitomi Pharmaceutical, "Pyrrolidine Compounds and Medicinal Utilization Thereof," May 11, 2000, English language machine translation of abstract, Espacenet, date obtained: Apr. 5, 2019, 2 pages.
WO2003078431, Bayer AG, "AZA-Bicyclic N-Biarylamides with Affinity for the Alpha-7 Nicotinic Acetylcholine Receptor," Sep. 25, 2003, English language machine translation of abstract, Espacenet, date obtained: Apr. 5, 2019, 2 pages.

* cited by examiner

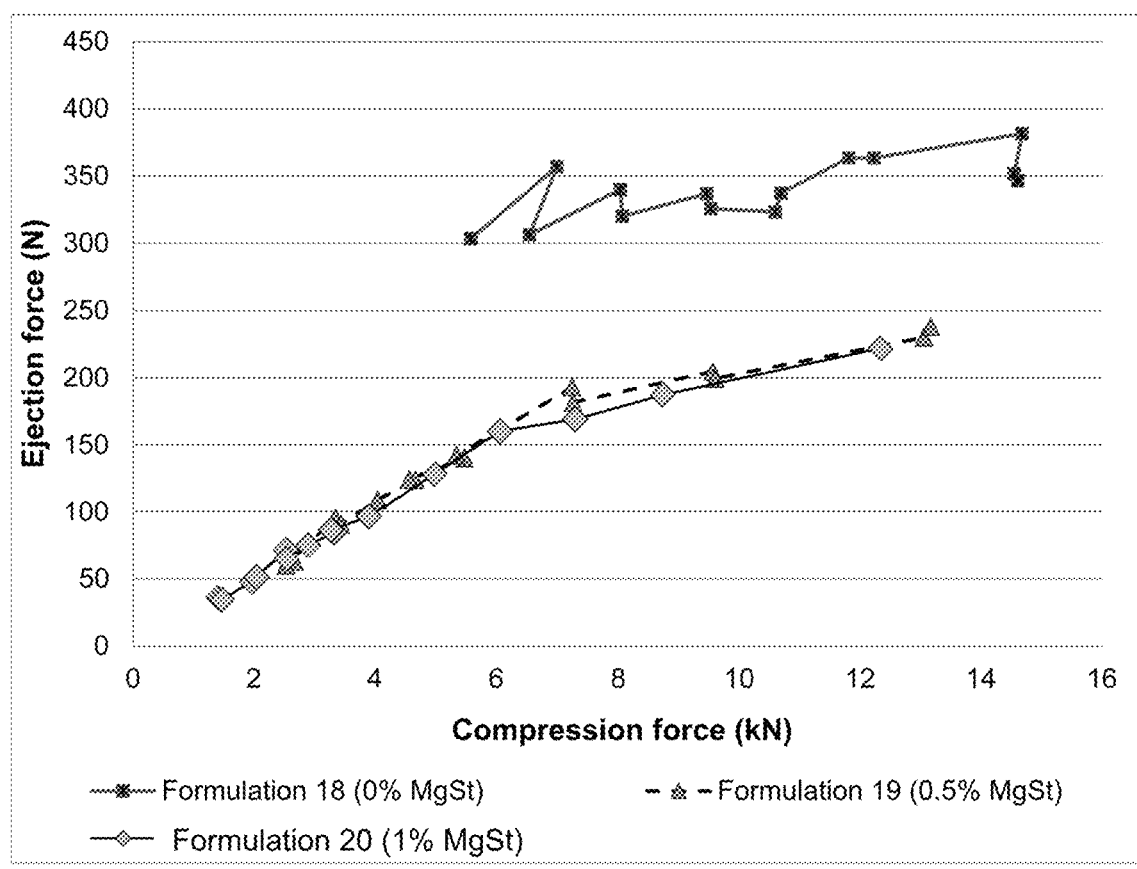

PHARMACEUTICAL COMPOSITIONS COMPRISING VENGLUSTAT

CROSS-REFERENCE TO RELATED APPLICATIONS

This application is a U.S. Non-Provisional Application under 35 U.S.C. § 111(a), which claims priority to and the benefit of U.S. Provisional Application Ser. No. 63/056,075, filed on Jul. 24, 2020, and European Application No. 21152595.1, filed on Jan. 20, 2021, the contents of each of which are hereby incorporated by reference in their entireties.

TECHNICAL FIELD

The present disclosure relates to pharmaceutical compositions, including dosage forms, such as tablets or capsules, comprising venglustat, in free base, or pharmaceutically acceptable salt form, optionally in combination with one or more additional therapeutic agents, processes for manufacture thereof, and methods of use in the treatment or prevention of disease.

BACKGROUND OF THE INVENTION

Quinuclidine compounds such as venglustat have activity as inhibitors of the enzyme glucosylceramide synthase (GCS). These compounds have been disclosed as generally being useful in the treatment lysosomal storage diseases such as Fabry disease, Gaucher disease, and Niemann-Pick disease. See, e.g., WO 2012/129084 and U.S. 2016/0361301. Other diseases which may be treated using GCS inhibition are polycystic kidney disease, especially autosomal dominant polycystic kidney disease or ADPKD (e.g., WO 2014/152215), proteinopathies such as Alzheimer's disease, and Parkinson's disease (e.g., WO 2016/145046), and ciliopathies such as Bardet-Biedl syndrome (BBS) and Joubert syndrome (e.g., PCT/US2020/016588, published as WO 2020/163337).

For example, Gaucher disease (GD) is a rare, autosomal recessive, lysosomal storage disease. GD patients have a mutation in the GBA1 gene which encodes glucosylceramidase (GC), also known as beta-glucocerebrosidase. This enzyme is responsible for breaking down glycosphingolipids into their components, such as breaking down glucosylceramide (GLC; also known as glucocerebroside) into glucose and ceramide. Monocytes and macrophages have a particularly high content of lysosomes containing GLC, and in GD patients these cells become enlarged and accumulate toxic concentrations of GLC. These so-called "Gaucher cells" accumulate in several organs, including the bone, bone marrow, spleen, liver, lung, and brain. Systemically, this results in splenomegaly, hepatomegaly, anemia, thrombocytopenia, leukopenia, osteopenia, osteonecrosis, and other pathologic abnormalities.

Type 1 Gaucher disease (GD-1), non-neuronopathic GD, is the most common form, with median age at diagnosis of 28, and mildly reduced life expectancy. In GD-1, the GC enzyme retains some functionality, and there is no neurological involvement. Type-2 GD is acute neuronopathic GD, with diagnosis during infancy, severe neurological involvement, and death usually within the first two years of life. The GC enzyme in a Type-2 patient is more severely compromised in function compared to in GD-1. Type-3 GD is chronic neuronopathic GD, with diagnosis during childhood, gradually worsening neurological involvement, and life expectancy usually not more than 30 years. Symptoms of GD-3 include spleen and liver abnormalities, fatigue, bleeding, seizures, and supranuclear gaze palsy. The neurological manifestations in GD-3 patients gradually develops over the course of the disease.

Existing treatment for GD-1 and GD-3 are limited to recombinant enzyme replacement therapy (ERT) using imiglucerase, velaglucerase, or taliglucerase, and substrate reduction therapy (SRT) using miglustat or eliglustat. Imiglucerase, the leading treatment regimen, is a recombinant version of human GC, made in Chinese hamster ovary cells and administered by slow intravenous injection (typically over 1-2 hours) every 1-2 weeks. It has been available since 1998 in the U.S. Velaglucerase is another recombinant human GC analog, this one made in a fibrosarcoma cell line, and it was FDA-approved in 2010. Taliglucerase is similar, made using genetically modified carrot plant root cells, and has been approved since 2012. These treatments all require IV administration in a hospital or other medical setting and the recombinant enzymes do not cross the blood-brain barrier, and therefore, are not capable of treating the neurological symptoms of GD. Thus, while these ERT regimes have proven effective in treating GD-1 patients, in GD-3 patients they are only effective in treating the non-neurological symptoms of the disease.

Substrate-reduction therapy is an alternative approach to treating GD. The goal of this therapy is to reduce the accumulation of GLC by inhibiting the enzyme which is responsible for synthesizing GLC. Glucosylceramide synthase (GCS), also known as UDP-glucose ceramide synthase, is the enzyme which catalyzes the initial glycosylation step of ceramide to form glucosylceramide.

Venglustat is (S)-quinuclidin-3-yl 2-(2-(4-fluorophenyl) thiazol-4-yl)propan-2-ylcarbamate, having the following structure:

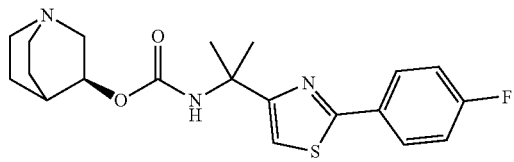 [SMILES: CC(C)(NC(=O)O[C@@H]1CN2CCC1CC2)c1csc(-c2ccc(F)cc2)n1]

However, there remains an urgent need for an orally available pharmaceutical formulation to treat these debilitating diseases.

BRIEF SUMMARY OF THE INVENTION

The present disclosure provides oral pharmaceutical compositions, including dosage forms, comprising venglustat in free base or pharmaceutically acceptable salt form, such as, in combination with one or more pharmaceutically acceptable excipients. In some embodiments, the dosage form is a tablet. In other embodiments, the dosage form is a capsule. In some embodiments the dosage form further comprises one or more additional therapeutic agents. These compositions are useful for the treatment or prevention of a variety of diseases and disorders related to dysfunctional sphingolipid storage and processing.

BRIEF DESCRIPTION OF THE DRAWINGS

FIG. 1 shows the results of an assessment of compression and ejection force characteristics in the formation of tablets from compositions described herein by direct compression using a Stylcam compaction simulator (equipped with 7 mm punches).

DETAILED DESCRIPTION

The present disclosure provides venglustat formulated for oral administration, particularly for patients suffering from diseases including Fabry disease, Gaucher disease, Parkinson's disease, and polycystic kidney disease. Patients for venglustat include children, as well as adults with motor dysfunction. While most patients in need of venglustat will take a solid oral dosage form by swallowing, with or without liquid, some patients in need of venglustat have difficulty swallowing traditional oral dosage forms. The present disclosure therefore provides oral dosage forms which are safe and suitable for use in children and in patients with difficulty swallowing, including chewable tablets and orally disintegrating tablets. In particular, some tablets according to the present invention can be swallowed whole by most patients, but may also be chewed by patients with swallowing difficulty (in contrast to many chewable tablets which must be chewed for effective absorption). The formulations according to the present disclosure meet the following requirements: good physical and chemical stability (i.e., compatibility between the ingredients), suitability for direct compression tableting, adherence to U.S. FDA requirements for chewability, palatability, fast disintegration, suitable resistance to crushing, and suitable friability. Because patients with swallowing difficulty may prefer to chew the tablets, the tablets are preferably formulated for effective chewability with respect to taste, mouthfeel, and hardness. Preferably, chewable tablets have a chewing difficulty index of less than 0.6 Nm, which is considered satisfactory for this such a patient population (including pediatric patients and adult patients with motor abnormalities). In addition, compositions according to the present disclosure provide acceptable taste and mouthfeel, with acceptable hardness and friability for chewing, while also retaining acceptable physical properties for effective manufacturing (such as avoiding stickiness to process machinery) and rapid aqueous dissolution for immediate drug delivery.

Venglustat is a tertiary amine compound comprising a quinuclidine ring. The ring nitrogen in a quinuclidine ring is relatively highly reactive due to the geometry of the constrained ring system. One result of this is that quinuclidine undergoes relatively facile N-oxidation to form Compound A:

Compound A

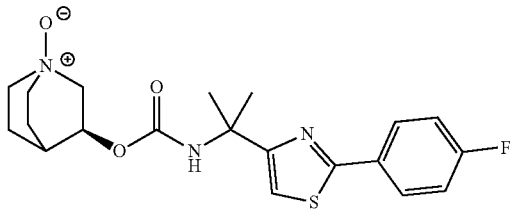

The gradual formation of this degradation product makes formulation of oral dosage forms for venglustat difficult, as it is necessary to provide a sufficiently inert environment for the venglustat so as to minimize the formation of this N-oxide compound, both during formation of the API and its incorporation into final dosage forms and during storage of the resulting dosage forms.

The present disclosure provides an oral pharmaceutical composition (Composition 1), comprising venglustat:

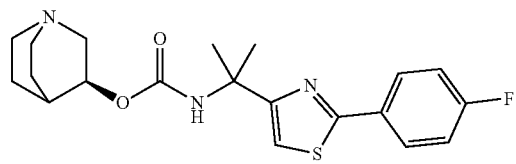 [SMILES: CC(C)(NC(=O)O[C@@H]1CN2CCC1CC2)c1csc(-c2ccc(F)cc2)n1]

in free base or pharmaceutically acceptable salt form (e.g., in malate salt form), a diluent/filler (e.g., cellulose or microcrystalline cellulose, mannitol, or lactose), and a lubricant (e.g., magnesium stearate or sodium stearyl fumarate). For example, Composition 1 may be as follows:

1.1. Composition 1, wherein the Composition comprises the venglustat in free base form;
1.2. Composition 1, wherein the Composition comprises the venglustat in pharmaceutically acceptable salt form;
1.3. Composition 1.2, wherein the Composition comprises the venglustat in an acid addition salt form;
1.4. Composition 1.3, wherein said acid addition salt form is a salt selected from the hydrochloride, hydrobromide, hydroiodide, nitrate, sulfate, bisulfate, phosphate, acid phosphate, acetate, lactate, citrate, acid citrate, tartrate, bitartrate, succinate, hydroxysuccincate, malate, maleate, fumarate, gluconate, saccharate, benzoate, methanesulfonate, and pamoate;
1.5. Composition 1.4, wherein the acid addition salt form is selected from hydrochloride, hydroxysuccinate (e.g., 2-hydroxysuccinate), and malate;
1.6. Any of Compositions 1 or 1.1-1.5, wherein the Composition comprises the venglustat in the form of a hydrate, solvate, and/or polymorph (such as an anhydrous polymorph);
1.7. Any of Compositions 1.1-1.6, wherein the venglustat is in solid crystal form (e.g., crystalline malate salt Form A of venglustat);
1.8. Any of Compositions 1.1-1.6, wherein the venglustat is in solid amorphous form;
1.9. Composition 1 or any of 1.1-1.8, wherein the Composition is a bulk solid (such as a powder) for use in the formation of an oral dosage form;
1.10. Composition 1 or any of 1.1-1.8, wherein the Composition is a finished dosage form, e.g., a capsule (e.g., a hard capsule) or a tablet (e.g., a chewable tablet, orally-disintegrating tablet, dispersible tablet, or a classic tablet or caplet), optionally wherein said finished dosage form comprises from about 2 to about 30 mg of venglustat (measured as the equivalent amount of free base), e.g. from about 4 mg to about 20 mg, or from about 8 mg to about 12 mg, or about 4 mg, or about 6 mg, or about 8 mg, or about 12 mg, or about 15 mg of venglustat (measured as the equivalent amount of free base);
1.11. Composition 1.10, wherein the dosage form is a classic tablet (e.g., for swallowing), a chewable tablet, an orally-disintegrating tablet, or a dispersible tablet;
1.12. Composition 1 or any of 1.1-1.11, wherein the Composition further comprises one or more additional pharmaceutically acceptable excipients;

1.13. Composition 1.12, wherein the one or more additional pharmaceutically acceptable excipients comprises one or more of diluent/filler (e.g., cellulose or microcrystalline cellulose, mannitol, or lactose), binder (e.g., povidone, methylcellulose, ethylcellulose, hydroxypropyl cellulose (such as low-substituted hydroxypropyl cellulose), or hydroxypropyl methylcellulose), disintegrant (e.g., crospovidone, sodium starch glycolate, or croscarmellose sodium), lubricant (e.g., magnesium stearate or sodium stearyl fumarate), a glidant (e.g., silica or talc), sweetener (e.g., sucralose, acesulfame potassium, aspartame, saccharine, neotame, or advantame), flavor (e.g., apricot flavor), and dye or colorant; for example, where the one or more additional pharmaceutically acceptable excipients comprises one or more of binder, disintegrant, a glidant, sweetener, flavor, and dye or colorant;

1.14. Composition 1.12 or 1.13, wherein the one or more pharmaceutically acceptable excipients comprises one or more hydrophilic water-soluble or water swellable polymers;

1.15. Composition 1.14, wherein the polymer is selected from the group consisting of natural or modified cellulosic polymers, or any mixture thereof;

1.16. Composition 1 or any of 1.1-1.15, wherein the Composition comprises or consists of (a) venglustat (e.g., venglustat malate), (b) the diluents/fillers mannitol and/or cellulose (e.g., microcrystalline cellulose), (c) the lubricants magnesium stearate and/or sodium stearyl fumarate, (d) the disintegrants croscarmellose sodium and/or crospovidone, (e) the binders povidone, ethylcellulose, and/or hydroxypropyl cellulose (e.g., low-substituted hydroxypropyl cellulose), (f) the glidant silica (e.g., colloidal and/or anhydrous silica), and (g) flavor, sweetener and/or color;

1.17. Composition 1.10, or any of 1.12-1.15 when dependent thereon, wherein the Composition is a capsule (e.g., a hard-walled capsule), comprising or consisting of (a) venglustat (e.g., venglustat malate), (b) the diluents/filler cellulose (e.g., microcrystalline cellulose), (c) the lubricant magnesium stearate, (d) the disintegrant croscarmellose sodium, (e) the glidant silica (e.g., colloidal and/or anhydrous silica), (f) flavor, sweetener, and/or color (e.g., titanium dioxide and/or red iron dioxide, such as in the capsule shell), and (g) a capsule shell (e.g., a gelatin shell);

1.18. Composition 1.10, or any of 1.12-1.15 when dependent thereon, wherein the Composition is a tablet (e.g., a chewable tablet, orally-disintegrating tablet, dispersible tablet, or a classic tablet or caplet), comprising or consisting of (a) venglustat (e.g., venglustat malate), (b) the diluents/fillers mannitol and/or cellulose (e.g., microcrystalline cellulose), (c) the lubricants magnesium stearate and/or sodium stearyl fumarate, (d) the disintegrants croscarmellose sodium and/or crospovidone, (e) the binders povidone, ethylcellulose, and/or hydroxypropyl cellulose (e.g., low-substituted hydroxypropyl cellulose), (f) the glidant silica (e.g., colloidal and/or anhydrous silica), and (g) flavor, sweetener and/or color;

1.19. Composition 1.18, wherein the Composition is a tablet (e.g., a chewable tablet, orally-disintegrating tablet, dispersible tablet, or a classic tablet or caplet), comprising or consisting of (a) venglustat (e.g., venglustat malate), (b) the diluent/filler mannitol, (c) the lubricants magnesium stearate and sodium stearyl fumarate, (d) the disintegrant crospovidone, (e) the binder hydroxypropyl cellulose (e.g., low-substituted hydroxypropyl cellulose), (f) the glidant anhydrous colloidal silica, and (g) flavor, sweetener and/or color;

1.20. Any of Compositions 1.12-1.19, wherein any one or more of each said diluent/filler, said lubricant, and said additional pharmaceutically acceptable excipients are present in an amount of 0.01 to 80% by weight of the Composition, e.g., 0.1 to 60%, or 0.1 to 40%, or 0.1 to 30%, 0.01 to 15%, or 0.01 to 10%, or 0.1 to 20%, or 0.1 to 15% or 0.1 to 10%, or 0.5 to 10%, or 0.5 to 5%, or 1 to 5%, or 2.5 to 5%, or 1 to 3%, or 0.1 to 1%;

1.21. Any of Compositions 1.12-1.20, wherein the Composition comprises (a) from 3% to 20% by weight of venglustat (e.g., venglustat malate), measured as the free base equivalent, e.g., 5 to 15%, or 4 to 8%, or 10 to 20%, or 7.5 to 12.5%, or about 4%, or about 10%, or about 15%; (b) from 60-95% by weight of diluent(s)/filler(s), e.g., 60-70% or 70-80%, or 65-75%, or 65-70%, or about 68%; (c) from 0.5-5% by weight of lubricant(s), e.g., 1-5%, or 2-4%, or 2-3%, or about 3%; (d) from 2-15% by weight of disintegrant(s), e.g., 4-12%, or 6-10%, or 7-9%, or about 8%; (e) from 0-12% by weight of binder(s), e.g., 2-10%, or 2-8%, or 3-7%, or 4-6%, or about 5%; (f) from 0-5% by weight of glidant(s), e.g., 0.15-4%, or 1-3%, or 1-2%, or about 1%; and (g) from 0-2% by weight of flavor(s), 0-2% by weight of sweetener(s), and/or 0-2% by weight of color(s), e.g., about 1% each of flavor(s), sweetener(s), and/or color(s);

1.22. Any of Compositions 1.12-1.20, wherein the Composition comprises (a) from 3% to 20% by weight of venglustat (e.g., venglustat malate), measured as the free base equivalent; (b) from 60 to 90% by weight of diluent(s)/filler(s), e.g., 60 to 70%; (c) from 0.5-6% by weight of lubricant(s), e.g., 2-4%; (d) from 2-15% by weight of disintegrant(s), e.g., 6-10%; (e) from 1-12% by weight of binder(s), e.g., 2-6%; (f) from 0-5% by weight of glidant(s), e.g., 0.5-1.5%; and (g) from 0-2% by weight of flavor(s), 0-2% by weight of sweetener(s) and/or 0-2% by weight of color(s), e.g., about 1% each of flavor(s), sweetener(s), and/or color(s);

1.23. Any of Compositions 1.1-1.16 or 1.18-1.22, wherein the Composition is a tablet comprising a mixture of venglustat (e.g., venglustat malate), said diluent/filler, said lubricant, and said one or more additional pharmaceutically acceptable excipients;

1.24. Composition 1.23, wherein the tablet is formed by direct compression of a mixture of venglustat (e.g., venglustat malate), said diluent/filler, said lubricant, and said one or more additional pharmaceutically acceptable excipients;

1.25. Any of Compositions 1.23 or 1.24, wherein the Composition comprises or consists of (a) from 7.5-12.5% by weight of venglustat (e.g., venglustat malate), measured as the free base equivalent; (b) from 60 to 90% by weight of mannitol e.g., 60 to 70%; (c) from 0.5-6% by weight of sodium stearyl fumarate and magnesium stearate, e.g., 2-4%; (d) from 2-15% by weight of crospovidone, e.g., 6-10%; (e) from 1-12% by weight of hydroxypropyl cellulose (e.g., low-substituted), e.g., 2-6%; (f) from 0-5% by weight of anhydrous colloidal silica, e.g., 0.5-1.5%; and (g) from 0-2% by weight of flavor(s), 0-2% by weight of sweetener(s) and/or 0-2% by weight of color(s), e.g., about 1% each of flavor(s), sweetener(s), and/or color(s);

1.26. Composition 1.25, wherein the composition comprises or consists of (a) venglustat malate in an amount from about 9-11% by weight of venglustat free base equivalent; (b) from 60 to 75% by weight of mannitol, e.g., 65 to 70%; (c) from 1.5-3% by weight of sodium stearyl fumarate, e.g. 2-3%, and 0.1-3% magnesium stearate, e.g., 0.1-1% or 0.25-1%; (d) from 3-15% by weight of crospovidone, e.g., 7-9%; (e) from 2-8% by weight of hydroxypropyl cellulose (e.g., low-substituted), e.g., 4-6%; (f) from 0.1-3% by weight of anhydrous colloidal silica, e.g., 0.5-1.5%; (g) from 0.5-1.5% by weight of flavor; and (h) from 0-2% by weight of sweetener;

1.27. Any of Compositions 1.12-1.17 or 1.20-1.22, wherein the Composition is a hard-shelled capsule, e.g., wherein said capsule contains a mixture of venglustat (e.g., venglustat malate) and the any one or more pharmaceutically acceptable excipients, and said venglustat and said one or more pharmaceutically acceptable excipients (e.g., other diluents/carriers) are comprised as granules or pellets, or as a powder, said granules, pellets or powder being contained within the shell of the capsule;

1.28. Any preceding Composition wherein the venglustat is present in (a) a mean particle size of 5 to 150 μm, e.g., 5 to 120 μm, 5 to 100 μm, 10 to 100 μm, 15 to 85 μm, 20 to 60 μm, or 30 to 40 μm; and/or (b) a D90 of 120 μm or less, e.g., 50 to 100 μm, 70 to 90 μm, or 60 to 80 μm; and/or (c) a D10 of 30 μm or less, e.g., 10 to 25 μm, 10 to 20 μm or less, or 11 to 14 μm;

1.29. Any foregoing Composition, wherein the Composition further comprises an effective amount of one or more additional therapeutic agents;

1.30. Composition 1.29, wherein the additional therapeutic agent is a GCS inhibitor;

1.31. Composition 1.29, wherein the additional therapeutic agent is miglustat, eliglustat, or migalastat;

1.32. Any preceding Composition, wherein the ingredients of the Composition are mixed using a dry-blending (e.g., for tablets) or dry-granulating process (e.g., for capsules, such as by roller compaction);

1.33. Any preceding Composition, wherein the Composition is intended to be administered once daily, or twice daily, or three times daily, or every other day, or every third day;

1.34. Any preceding Composition, wherein the Composition is packaged in a blister pack (e.g., push-through pack), e.g., a blister pack made of any suitable material (e.g., aluminum foil, polyvinyl chloride, polyvinylidene chloride, polychlorotrifluoroethylene, cyclic olefin copolymers, polyethylene, polypropylene, polyethylene terephthalate, or a combination thereof);

1.35. Any preceding Composition, wherein the Composition is packaged in a blister pack made of aluminum foil;

1.36. Any preceding Composition, wherein the Composition is formulated for immediate-release;

1.37. Any preceding Composition, wherein the Composition provides at least 80% dissolution within 15 minutes (e.g., using FDA and/or EMEA immediate-release solid oral dosage form testing guidelines), such as in pH 1.2 (HCl), pH 4.5 (acetate buffer), or pH 6.8 (phosphate buffer) dissolution medium, for example 85-100% dissolution, or 95-100% dissolution;

1.38. Any preceding Composition, wherein the Composition provides at least 70% dissolution within 5 minutes (e.g., using FDA and/or EMEA immediate-release solid oral dosage form testing guidelines), such as in pH 1.2 (HCl), pH 4.5 (acetate buffer), or pH 6.8 (phosphate buffer) dissolution medium, for example 75-100% dissolution, or 85-100% dissolution, or 95-100% dissolution;

1.39. Any preceding Composition, wherein the Composition is a dosage form appropriate for pediatric use (e.g., comprising about 4-6 mg of venglustat (e.g., venglustat malate), based on the equivalent free base amount), such as a tablet of <8 mm in length, width, or diameter (e.g., 3-7 mm in length, width, or diameter, or 3-5 mm in width or diameter, or 3-4 mm in width);

1.40. Any preceding Composition, wherein the composition comprises less than or equal to 0.50% by weight of the Compound A (e.g., as measured by HPLC or UPLC), for example, less than or equal to 0.20% by weight or less than or equal to 0.10% by weight of Compound A;

1.41. Any preceding Composition, wherein the composition comprises from 0.001 to 0.10% by weight, or from 0.01 to 0.10% by weight, of Compound A (e.g., as measured by HPLC or UPLC);

1.42. Any preceding Composition, wherein the composition comprises unspecified degradation products in an amount of no more than 0.20% by weight individually (e.g., as measured by HPLC or UPLC), for example in an amount of no more than 0.10% by weight individually;

1.43. Any preceding Composition, wherein the composition comprises no more than 1.5% by weight of total degradation products collectively (including Compound A).

1.44. Any preceding Composition, wherein the composition is chemically and/or physically stable for a period of at least 6 months, or 12 months, or 18 months, 24 months, or 36 months, for example, based on HPLC or UPLC assay to monitor the formation of Compound A and unspecified degradation products.

1.45. A Composition according to Composition 1.44, where the composition comprises less than or equal to 0.50% by weight, such as less than or equal to 0.20% by weight, or less than or equal to 0.10% by weight, of the Compound A (e.g., as measured by HPLC or UPLC) for a period of at least 6 months, or 12 months, or 18 months, 24 months, or 36 months (for example, when stored at 30° C. and 65% relative humidity);

1.46. Any preceding Composition, except for Compositions 1.17 or 1.27, wherein the Composition is a chewable tablet (e.g., a tablet with a chewing difficulty index of less than 0.6 Nm, or less than 0.5 Nm, or less than 0.4 Nm, or less than 0.2 Nm), e.g., as described in Gupta et al., "An index for evaluating difficulty of Chewing Index for chewable tablets" *Drug Develop. & Indus. Pharmacy,* 41:2, 239-243 (2015), optionally wherein the chewable tablet may also be swallowed whole (e.g., as for a classic tablet);

1.47. Composition 1.46, wherein the Composition is a chewable tablet having about 4 mg or about 6 mg of venglustat (e.g., venglustat malate), based on the equivalent free base amount, and a chewing difficulty index of less than 0.2 Nm; or 1.48. Composition 1.46, wherein the Composition is a chewable tablet having about 15 mg of venglustat (e.g., venglustat malate), based on the equivalent free base amount, and a chewing difficulty index of less than 0.5 Nm.

In some embodiments, binders may include one or more of hydroxypropyl cellulose, hydroxypropyl methylcellulose, ethyl cellulose, methylcellulose, polyvinyl pyrrolidone (povidone), cross-linked polyvinylpyrrolidone (crospovidone), polyvinyl alcohol, gum arabic powder, gelatin, pullulan, and the like.

In some embodiments, disintegrants may include one or more of carmellose calcium, croscarmellose sodium, sodium starch glycolate, cross-linked polyvinylpyrrolidone (crospovidone), hydroxypropyl cellulose, powdered agar, and the like.

In some embodiments, the pharmaceutical compositions of the present disclosure further comprise an appropriate amount of a flavor, a lubricant, a coloring agent, and the like, or various additives which are commonly used for preparing a galenic formulation. For capsule dosage forms, any of such additives may be comprised in the capsule shell, or within the capsule, or both. If comprised within the capsule, such additives may be incorporated within the granules, pellets, or powder material which comprises the venglustat, or such additives may be comprised in granules, pellets, or powder material separate from the granules, pellets, or powder comprising the venglustat.

In some embodiments, lubricants may include magnesium stearate, calcium stearate, sucrose fatty acid ester, polyethylene glycol, talc, stearic acid, sodium stearyl fumarate, and the like. In some embodiments, coloring agents may include the food colors such as food yellow no. 5, food red no. 2, food blue no. 2, food lake colors, titanium dioxide, iron sesquioxide, and the like.

Tablets may be round, square, rectangular, spherical, oblong, oblate, oval, or any other suitable shape, including capsule-shaped (i.e., caplets). Tablets may optionally be scored for easier cutting, and may optionally be engraved.

Hard-shelled capsules are two-piece gel encapsulations of solid material. The capsule shell consists of two halves, an outer half and an inner half, which when joined and sealed form a secure enclosure for the solid material contained therein. The active pharmaceutical ingredient, e.g., the venglustat, may be comprised as a powder, or as one or more granules or pellets within the capsule. Such granules or pellets may be manufactured by any suitable means, including roller compaction.

When packaged as active pharmaceutical ingredient (API), compositions of the present disclosure are typically provided as powders (either fine or coarse) and packaged into sterile containers, such as bags or drums.

In some embodiments, coloring agents may be used to introduce a uniformity of appearance to the product and/or to protect any light-sensitive ingredients. Suitable coloring agents include all pigments, dyes, and lakes approved by the U.S. Food and Drug Administration (e.g., FD&C colorants), including but not limited to FD&C Yellow #6, FD&C Blue #1, FD&C Red #3, black iron oxide, red iron oxide, titanium dioxide, or any combination thereof. For capsules, coloring agents may be included within the capsule shell, within the capsule fill, or both.

In some embodiments, sweeteners may be used to mask unpleasant taste or to achieve a desired taste. Examples of sweetening agents are glucose, sorbitol, glycerol, sucralose, acesulfame potassium, aspartame, neotame, advantame, saccharin, and neohesperidin dihydrochalcon. The taste may be optimized further by the addition of one or more flavoring substances. Suitable flavoring substances are fruit flavors such as cherry, raspberry, black currant, lemon, apricot, or strawberry flavor or other flavors such as liquorice, anise, peppermint, caramel, and tutti frutti.

The compositions of the present disclosure can be prepared by dry granulating venglustat, in free base or pharmaceutically acceptable salt form, and one or more pharmaceutically acceptable excipients, for example, a binder (a disintegrant may be further contained), using a machine such as a roller compactor; blending a disintegrant (a lubricant may be further contained) to the granules; and then subjecting to encapsulation to form capsules or compression to form tablets.

Suitable forms of venglustat include the free base form, including amorphous solid dispersions thereof, pharmaceutically acceptable salt forms, including crystal forms thereof, and pharmaceutically acceptable co-crystal forms. Unless otherwise indicated, the term "pharmaceutically acceptable salt" includes acid addition salts between venglustat and any pharmaceutically acceptable acid (e.g., Bronsted acid) in any molar ratio permitted by the structure of the acid. In some embodiments, the salt is a crystalline solid (e.g., a salt crystal). In an embodiment, the crystalline salt form of venglustat is crystalline malate salt Form A as disclosed in, e.g., US 2016/0039805 (the content of which is hereby incorporated by reference in its entirety), with particular reference being made to paragraphs [0005] to [0010] and FIG. 1 of that document.

In a second aspect, the present disclosure provides a process (Process 1) for the manufacture of Composition 1, or any of 1.1-1.48, wherein the process comprises the steps of:

(a) sieving each ingredient (e.g., separately);
(b) combining venglustat, in free base or pharmaceutically acceptable salt form (e.g., malate salt form), with a diluent/filler (e.g., mannitol), and optionally with a glidant (e.g., silica), a lubricant (e.g., sodium stearyl fumarate), any colors or flavors, or any other excipients, or a combination thereof;
(c) blending and/or milling and/or granulating (e.g., dry granulating) the resulting the mixture;
(d) optionally filtering (e.g., screening) the resulting mixture;
(e) adding at least one other diluent or carrier to the mixture, such as additional diluent/filler (e.g., mannitol), a disintegrant (e.g., crospovidone), a binder (e.g., hydroxypropyl cellulose), a lubricant (e.g., sodium stearyl fumarate), or any other excipient, or a combination thereof, wherein, if a lubricant (e.g., sodium stearyl fumarate) is not combined with the venglustat and the diluent/filler in step (b), a lubricant (e.g., magnesium stearate) is added to the mixture;
(f) blending and/or milling and/or granulating (e.g., dry granulating) the resulting mixture;
(g) optionally filtering (e.g., screening) the resulting mixture;
(h) adding a lubricant (e.g., magnesium stearate) and any additional excipients;
(i) blending and/or milling the resulting mixture;
(j) optionally granulating (e.g., dry granulating) the resulting mixture;
(k) optionally filtering (e.g., screening) the resulting mixture;
(l) encapsulating the resulting material, e.g., into hard-walled capsules; or compressing the resulting material, e.g., to form a tablet;
(m) optionally applying one or more coatings to the capsule, tablet, or other dosage form; and
(n) optionally packaging the resulting finished dosage form, e.g., into aluminum foil blister packs.

In some embodiments, steps (i), (j), and/or (k) may be repeated for any additional excipients added in step (h) as necessary before proceeding to steps (l), (m), or (n).

The lubricant added in either of step (b) or step (e) may be the same or different to the lubricant added in step (h). In embodiments, a lubricant is combined with the venglustat and the diluent/filler in step (b).

In some embodiments, when the composition is a solid tablet, a lubricant is added in step (b) (e.g., sodium stearyl fumarate) and is different to the lubricant added in step (h) (e.g., magnesium stearate). Preferably, when the composition is a solid tablet, if magnesium stearate is added as a second lubricant, this lubricant should be added as the final excipient added before final mixing and compression to form the tablet. In some embodiments, when the composition is a capsule, a lubricant is added in step (e) (e.g., a first portion of magnesium stearate) and is the same as the lubricant added in step (h) (e.g., a remaining portion of magnesium stearate).

In some embodiments, the process comprises the following steps:
(a) sieving one or more ingredients (e.g., separately), for example, all ingredients, or only some ingredients (e.g., sieving half of the amount of microcrystalline cellulose, silica, and lubricant (magnesium stearate and/or sodium stearyl fumarate));
(b) combining venglustat malate with microcrystalline cellulose (a first portion), sucralose (if any), flavor (if any), and croscarmellose sodium, optionally wherein these ingredients are not previously sieved;
(c) blending and/or milling and/or granulating (e.g., dry granulating) the resulting the mixture;
(d) optionally sieving the resulting mixture;
(e) adding microcrystalline cellulose (second portion), silica, and a first portion of lubricant (magnesium stearate and/or sodium stearyl fumarate, e.g., a first portion of magnesium stearate, such as 15-50% by weight, or 20-30% by weight, of the total magnesium stearate lubricant added) to the mixture from step (c), optionally wherein these added ingredients are previously sieved from step (a);
(f) blending and/or milling and/or granulating (e.g., dry granulating) the resulting mixture;
(h) sieving the remaining portion of lubricant (e.g., magnesium stearate and/or sodium stearyl fumarate, such as a remaining portion of magnesium stearate—for instance, 50-85% by weight, or 70-80% by weight, of the total magnesium stearate lubricant added), and/or adding it to the mixture from step (f);
(i-j) blending and/or milling and/or granulating (e.g., dry granulating) the resulting mixture;
(l) filling the resulting material into hard capsules (e.g., size 3 capsules); and
(n) optionally packaging the resulting finished dosage form, e.g., into polymer film blister packs (e.g., polypropylene, polyvinyl chloride, polyethylene terephthalate, and/or polychlorotrifluoroethylene).

In some embodiments, the process comprises the following steps:
(a) sieving each of mannitol (a first portion thereof), silica, venglustat malate, sucralose (if any), flavor, and sodium stearyl fumarate (e.g., separately);
(b) combining the venglustat malate with the sieved mannitol, silica, sucralose (if any), flavor, and sodium stearyl fumarate (e.g., in amount to provide a composition comprising from 2-3% by weight sodium stearyl fumarate), optionally wherein each ingredient is sieved sequentially into a common container (e.g., tank or bag) to combine the ingredients;
(c) blending and/or milling and/or granulating (e.g., dry granulating) the resulting mixture;
(e) sieving mannitol (second portion), low-substituted hydroxypropyl cellulose, and crospovidone, and adding these sieved ingredients to the mixture from step (c);
(f) blending and/or milling and/or granulating (e.g., dry granulating) the resulting mixture;
(h) sieving magnesium stearate and adding it to the mixture from step (f) (e.g., in an amount to provide a composition comprising 0.1-1% by weight of magnesium stearate);
(i-j) blending and/or milling and/or granulating (e.g., dry granulating) the resulting mixture;
(l) compressing the resulting material to form a tablet; and
(n) optionally packaging the resulting finished dosage form, e.g., into aluminum foil blister packs.

In some embodiments, the process optionally further includes one or more dry granulation steps (e.g., roller compaction or slugging) which serve to increase the size of solid particles from powder-scale to granule-scale. In some embodiments, one or more blending steps may further include running the blend through a roller compactor, and optionally then milling the roller compacter ribbons. In some embodiments, any dry granulation step may be followed by a blending step to blend the resulting granules with one or more other excipients (e.g., lubricant).

In a third aspect, the present invention provides a composition prepared, or preparable, by Process 1, or any embodiments thereof, as described herein.

In a fourth aspect, the present disclosure provides a method (Method 1) for the treatment or prevention of a disease or disorder susceptible to treatment by GCS inhibition, comprising administering to a patient in need thereof an effective amount of Pharmaceutical Composition 1 or any of 1.1-1.48.

In a fifth aspect, the present disclosure provides a pharmaceutical composition, e.g., Composition 1 or any of 1.1-1.48, for use in the treatment or prevention of a disease or disorder susceptible to treatment by GCS inhibition.

In some embodiments, said disease or disorder susceptible to treatment by GCS inhibition is a lysosomal storage disease, e.g., Gaucher disease type 2 or type 3. In some embodiments, said disease or disorder is selected from polycystic kidney disease (PKD), especially autosomal dominant polycystic kidney disease (ADPKD), Gaucher disease, Fabry disease, Alzheimer's disease, Parkinson's disease, Bardet-Biedl Syndrome, Joubert syndrome, GM2, GM3, or any other disease or disorder as disclosed in any of US 2014/0255381, US 2015/0210681, US 2016/0039806, US 2016/0361301, US 2018/0036295, PCT/US2020/016588 (published as WO 2020/163337), PCT/US2020/016440 (published as WO 2020/163244), and PCT/US2020/016441 (published as WO 2020/163245), the contents of each of which are hereby incorporated by reference in their entireties.

The words "treatment" and "treating" are to be understood accordingly as embracing prophylaxis and treatment or amelioration of symptoms of disease and/or treatment of the cause of the disease. In particular embodiments, the words "treatment" and "treating" refer to prophylaxis or amelioration of symptoms of the disease.

The term "patient" may include a human or non-human patient.

Methods of synthesizing venglustat and its salts and polymorphs are known in art, and include the methods disclosed in US 2016/0039805, US 2014/0255381, US 2015/0210681, US 2016/0039806, US 2016/0361301, and US 2018/0036295, the contents of each of which are hereby incorporated by reference in their entireties.

Isolation or purification of the diastereomers of the Compounds of the Invention may be achieved by conventional methods known in the art, e.g., column purification, preparative thin layer chromatography, preparative HPLC, crystallization, trituration, simulated moving beds, and the like.

The pharmaceutically acceptable salts of venglustat can be synthesized from the free base compound, which contains basic moieties, by reaction with a suitable acid, by conventional chemical methods. Generally, such salts can be prepared by reacting the free base forms of these compounds with a stoichiometric amount of the appropriate acid in water, or in an organic solvent, or in a mixture of the two; generally, non-aqueous media like ether, ethyl acetate, ethanol, isopropanol, or acetonitrile are preferred.

Dosages employed in practicing the present disclosure will of course vary depending, e.g., on the particular disease or condition to be treated, the particular active compounds used, the mode of administration, the age of the patient (e.g., adult versus pediatric), the ability of the patient to swallow an oral dosage form, and the therapy desired. Unless otherwise indicated, an amount of an active compound for administration (whether administered as a free base or as a salt form) refers to or is based on the amount of the compound in free base form.

For the avoidance of doubt, any disclosure of a numerical range, e.g., "up to X" amount is intended to include the upper numerical limit X. Therefore, a disclosure of "up to 60 mg" includes 60 mg. Analogously, any disclosure of a numerical range is also intended to include the lower numerical limit, e.g., "from A to", or "at least A". Therefore, a disclosure of "from 5 mg to 50 mg" or "at least 5 mg" includes 5 mg.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated, that all numerical designations are preceded by the term "about". The term "about" in connection with any numerical value designates a variability about that value within the conventional range. For example, the numerical value may vary by ±10%, 5%, ±1.0%, or ±0.5%. It also is to be understood, although not always explicitly stated, that the reagents described herein are merely exemplary and that equivalents of such are known in the art.

As used herein, where a quantity of a substance is described in terms of a %, this is intended to refer to "% by weight", unless otherwise indicated.

As used herein, the phrase "in the treatment or prevention of" (such as in the phrase "in the treatment or prevention of pain") is meant to be equivalent to the phrase "in a method of treating or preventing" (such as in the phrase "in a method of treating or preventing pain").

As used in the specification and claims, the singular form "a", "an", and "the" include plural references unless the context clearly dictates otherwise. For example, the term "a cell" includes a plurality of cells, including mixtures thereof. Unless specifically stated or obvious from context, as used herein, the term "or" is understood to be inclusive. The term "including" is used herein to mean, and is used interchangeably with, the phrase "including but not limited to."

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. Use of the term "comprising" herein is intended to encompass and disclose "consisting essentially of" and "consisting of."

The terms "subject", "individual" and "patient" are used interchangeably herein, and refer to a vertebrate, such as a mammal. Mammals include, but are not limited to, murines, rats, rabbit, simians, bovines, ovine, porcine, canines, felines, farm animals, sport animals, pets, equines, primates, and humans. In one embodiment, the mammals include horses, dogs, and cats. In one embodiment, the mammal is a human.

"Treating" or "treatment" of a disease includes: (1) inhibiting the disease, i.e., arresting or reducing the development of the disease or its clinical symptoms; and/or (2) relieving the disease, i.e., causing regression of the disease or its clinical symptoms.

"Preventing" or "prevention" of a disease includes causing the clinical symptoms of the disease not to develop in a patient that may be predisposed to the disease but does not yet experience or display symptoms of the disease.

The term "suffering" as it relates to the term "treatment" refers to a patient or individual who has been diagnosed with the disease. The term "suffering" as it relates to the term "prevention" refers to a patient or individual who is predisposed to the disease. A patient may also be referred to being "at risk of suffering" from a disease because of a history of disease in their family lineage or because of the presence of genetic mutations associated with the disease. A patient at risk of a disease has not yet developed all or some of the characteristic pathologies of the disease.

An "effective amount" or "therapeutically effective amount" is an amount sufficient to effect beneficial or desired results. An effective amount can be administered in one or more administrations, applications, or dosages. Consistent with this definition, as used herein, the term "therapeutically effective amount" is an amount sufficient to treat (e.g., improve) one or more symptoms associated with a disease or disorder disclosed herein.

As used herein, the term "pharmaceutically acceptable excipient" encompasses any of the standard pharmaceutical excipients, including diluents and carriers, to enable the venglustat, in free base form or a pharmaceutically acceptable salt form (e.g., malate), to be formulated for use in a medicinal preparation.

As used herein, the term "pharmaceutically acceptable salt" means a pharmaceutically acceptable acid addition salt or a pharmaceutically acceptable base addition salt of a currently disclosed compound that may be administered without any resultant substantial undesirable biological effect(s) or any resultant deleterious interaction(s) with any other component of a pharmaceutical composition in which it may be contained.

Venglustat is a chiral (e.g., optically active) compound having the (S) stereochemical orientation. Preferably, the (S)-isomer is present in an enantiomeric excess of at least about 5%, 10%, 25%, 40%, 70%, 80%, 90%, 95%, 97%, 98% or 99%, e.g., about 100%.

As used herein throughout, unless provided otherwise, the word "venglustat" means venglustat in free base form or in any pharmaceutically acceptable salt form.

Isotopically-labeled compounds are also within the scope of the present disclosure. As used herein, an "isotopically-labeled compound" refers to venglustat, including pharmaceutical salts thereof, as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

The reference works, patents, patent applications, and scientific literature, and other printed publications that are mentioned or referred to herein are hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

EXAMPLES

Venglustat and its salt forms, including venglustat malate, may be prepared according to the procedures described in WO 2012/129084, WO 2014/151291, WO 2014/152215, U.S. Pat. Nos. 9,126,993, 9,518,049, 9,682,975, 10,065,949, and 10,604,518, the contents of each of which are hereby incorporated by reference in their entireties. In particular, reference may be made to the preparation of crystalline venglustat malate Form A as described in, e.g., Examples 1 and 2 of U.S. Pat. No. 9,518,049.

Example 1: Traditional Capsule and Tablet Formulations

Venglustat malate is a BCS class 1 drug substance. In its crystalline Form A it is highly soluble in water (>50 mg/mL) and in aqueous buffers at pH from 1.2 to 6.8 (at least 10 mg/mL). It was desired to formulate an immediate-release solid oral dosage form. An improved dry-granulation manufacturing process was developed for preparing 4 and 15 mg hard-walled capsules, and 4, 6, and 15 mg tablets.

Development of Hard Capsules

Initial batches of hard capsules were prepared based on the following formulation:

| Capsule Formulation A | | |
|---|---|---|
| Ingredient | 4 mg Capsule (Wt. %) | 15 mg Capsule (Wt. %) |
| Venglustat Malate | 5.4% (5.38 mg) | 20.2% (20.16 mg) |
| Microcrystalline cellulose (diluent) | Q.S. (~90%) | Q.S. (~76%) |
| Croscarmellose sodium (disintegrant) | 3.0% | 3.0% |
| Colloidal silica (glidant) | 0.2% | 0.2% |
| Sodium stearyl fumarate (lubricant) | 1.0% | 1.0% |
| Capsule Fill Mass | 100 mg | 100 mg |
| Capsule Size | #3 | #3 |

Capsule Formulation A was prepared by following the following steps: (a) all components are individually sieved with a 1.2 mm screen mesh; (b) approximately half of the microcrystalline cellulose, the venglustat malate, and the croscarmellose sodium are combined and blended for 10 minutes at 10 rpm in a tumble blender; (c) the remaining microcrystalline cellulose, the silica, and approximately half of the sodium stearyl fumarate are added to the blend from step (b) and the mixture is tumble blended for 15 minutes at 10 rpm; (d) the mixture from step (c) is passed through a roller compacter with rotative integrated milling; (e) the remaining sodium stearyl fumarate is added to the granulate blend from step (d) and the mixture is tumble blended for 5 minutes at 10 rpm; and (f) the mixture is filled into size 3 opaque hard capsules to a fill weight of 100 mg per capsule.

Capsule Formulation A was found to be physically and chemically stable and to meet all other specifications. In filling the hard-shell capsules with the blended final drug substance, it was however observed that some degree of undesirable sticking of the blend to the capsule filling machinery occurs. Therefore, an improved Capsule Formulation B was developed, according to the following formulation:

| Capsule Formulation B | |
|---|---|
| Ingredient | 15 mg Capsule (Wt. %) |
| Venglustat Malate | 12.2% (20.16 mg) |
| Microcrystalline cellulose (diluent) | Q.S. (~83%) |
| Croscarmellose sodium (disintegrant) | 3.0% |
| Colloidal silica (glidant) | 0.2% |
| Magnesium stearate (lubricant) | 2.0% |
| Capsule Fill Mass | 165 mg |
| Capsule Size | #3 |

Capsule Formulation B was prepared according to the following steps: (a) approximately half of the microcrystalline cellulose, the venglustat malate, and the croscarmellose sodium are combined and blended for 10 minutes in a tumble blender at 10 rpm; (b) the resulting mixture is sieved in a rotating mill with a 1.2 mm screen; (c) the remaining microcrystalline cellulose, the silica, and approximately half of the magnesium stearate are sieved in a rotating mill with a 1.2 mm screen, and are then added to the blend from step (b); (d) the resulting mixture is tumble blended for 15 minutes at 10 rpm; (e) the mixture from step (d) is passed through a roller compacter with rotative integrated milling; (f) the remaining magnesium stearate is sieved with a 1.0 mm screen and is then added to the granulate blend from step (e) and the mixture is tumble blended for 5 minutes at 10 rpm; and (g) the mixture is filled into size 3 opaque hard capsules to a fill weight of 165 mg per capsule.

This improved formulation used 2.0% magnesium stearate as the lubricant, instead of 1.0% sodium stearyl fumarate, and used a larger total fill mass per capsule, with a correspondingly lower concentration of active ingredient and a higher concentration of diluent.

The dissolution profiles of 15 mg capsules according to Capsule Formulations A and B were compared under standard conditions (500 mL medium; stirred at 50 rpm for 60 minutes at 37° C. using a paddle apparatus). Three dissolution media were used: (1) aqueous HCl at pH 1.2; (2) aqueous acetate buffer at pH 4.5; and (3) aqueous phosphate buffer at pH 6.8. The percent dissolution results from 0 to 50 minutes are shown in the tables below (mean, n=12, % dissolved):

| Aqueous HCl (pH 1.2) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| A | 83.6 | 86.6 | 88.8 | 90.6 | 92.0 | 93.1 | 94.1 | 95.0 | 95.8 | 96.4 | 97.0 | 97.4 |
| B | 85.2 | 88.2 | 90.5 | 92.0 | 93.2 | 94.0 | 94.8 | 95.4 | 95.8 | 96.2 | 96.6 | 96.9 |

-continued

Aqueous Acetate (pH 4.5)

| Time (min): | 5 | 10 | 15 | 20 | 25 | 30 | 35 | 40 | 45 | 50 | 55 | 60 |
|---|---|---|---|---|---|---|---|---|---|---|---|---|
| A | 92.2 | 94.3 | 95.8 | 96.7 | 97.5 | 98.1 | 98.7 | 99.2 | 99.5 | 99.9 | 100 | 100 |
| B | 82.6 | 88.3 | 90.6 | 92.1 | 93.3 | 84.2 | 95.0 | 95.6 | 96.2 | 96.7 | 97.1 | 97.6 |

Aqueous Phosphate (pH 6.8)

| Time (min): | 5 | 10 | 15 | 20 | 25 | 30 | 35 | 40 | 45 | 50 | 55 | 60 |
|---|---|---|---|---|---|---|---|---|---|---|---|---|
| A | 83.3 | 87.4 | 89.4 | 90.9 | 92.2 | 93.2 | 94.1 | 94.9 | 95.5 | 96.0 | 96.5 | 97.0 |
| B | 83.8 | 89.5 | 91.3 | 92.6 | 93.6 | 94.3 | 94.9 | 95.4 | 95.9 | 96.3 | 96.6 | 96.9 |

Development of Tablets

The requirements for a tablet were as follows: physical and chemical stability (i.e., compatibility between the ingredients), suitability for direct compression tabletting, adherence to U.S. FDA requirements for chewability, palatability, fast disintegration (suitable as an immediate release drug substance), suitable resistance to crushing, and suitable friability.

Tablet development proceeded based upon the following selected excipients:

| | |
|---|---|
| Diluent/Fillers | Mannitol (sold under the trademark Pearlitol 100SD or Parteck M100) |
| | Microcrystalline cellulose (sold under the trademark Avicel PH102) |
| Lubricants | Sodium stearyl fumarate (sold under the trademark Pruv) |
| | Magnesium stearate (sold under the trademark Hyqual) |
| Disintegrants | Croscarmellose sodium (sold under the trademark Ac-Di-Sol) |
| | Crospovidone Type A (sold under the trademark Kollidon CL) |
| | Crospovidone Type B (sold under the trademark Polyplasdone XL) |
| | Crospovidone Type C (sold under the trademark Polyplasdone XL-10) |
| Binders | Povidone K25 (sold under the trademark Kollidon 25) |
| | Ethyl cellulose (sold under the trademark Aqualon T10) |
| | Low-sub Hydroxypropyl cellulose (sold under the trademark NBD22) |
| Glidant | Colloidal amorphous silica (sold under the trademark HDK N20 Pharma) |
| Sweetener | Sucralose |
| | Sweet Modulator (mix containing potassium acesulfam E950 (46.7%) and natural flavor) |
| Flavor | Apricot |

A variety of formulations were prepared which combine selections of the above excipients (at least one from each category) in various ratios. Among the formulations tested were the following (all values are in weight % and are given to 0 or 1 decimal places):

| Number: | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Venglustat malate | 13 | 13 | 13 | 13 | 13 | 13 | 13 | 13 | 13 | 13 | 13 | 13 | 13 | 13 |
| Pearlitol | 65 | 65 | 72 | 70 | 72 | 74 | | | 70 | 70 | | | | |
| Parteck | | | | | | | 72 | 70 | | | 70 | 60 | 74 | 70 |
| Avicel | | | | | | | | | | | | 10 | | |
| Ac-Di-Sol | 8 | | | | | | | | | | | | | |
| Kollidon CL | | 8 | 8 | 8 | | 8 | 8 | | | 8 | | 8 | 4 | 8 |
| Poly. XL | | | | | | | | | | | 8 | | | |
| Poly. XL-10 | | | | | | 8 | | 8 | 8 | | | | | |
| Povidone | 10 | 10 | 3 | | | 3 | 3 | | | | | | | |
| L-HPC | | | | 5 | | | | 5 | 5 | 5 | 5 | 5 | 5 | 5 |
| Aqualon T10 | | | | | 3 | | | | | | | | | |
| Pruv | 2.5 | 2.5 | 2.5 | 2.5 | 2.5 | | 2.5 | 2.5 | 2.5 | 2.5 | 2.5 | 2.5 | 2.5 | 2.5 |
| Hyqual | | | | | | 0.8 | | | | | | | | |
| Silica | 1 | 1 | 1 | 1 | 1 | 1 | 1 | 1 | 1 | 1 | 1 | 1 | 1 | 1 |

It was found that microcrystalline cellulose as the diluent tends to result in formulations with high stickiness. When mannitol is used as the diluent, a good mouthfeel is provided when the tablet is chewed.

While the use of each of the disintegrants was found to be successful, it was unexpectedly found that crospovidone type A (Kollidon CL) provides faster disintegration times than the other disintegrants. It was further found that using 8% crospovidone provides faster disintegration than 4% crospovidone.

While each of the binders was found to provide an acceptable formulation, it was unexpectedly found that the use of low-substituted HPC (hydroxypropyl cellulose) allows better control of overall tablet hardness. The high swelling speed of HPC also assists with rapid disintegration. In addition, povidone was not retained as it was found that the use of povidone results in tablets which will progressively harden during aging.

With respect to the choice of lubricant, the first round of testing suggested that magnesium stearate (Hyqual) could not be used, and the majority of testing was performed using sodium stearyl fumarate (Pruv) instead. In contrast to the effective use of magnesium stearate in the hard-capsule formulations, it was found that tablet batches having magnesium stearate as the lubricant caused excessive sticking during tabletting.

However, these initial experiments were conducted with the lubricant added to the composition in a single first mixing step with the other excipients. Further development of the formula and manufacturing process unexpectedly revealed that better results could be obtained by using sodium stearyl fumarate lubricant in a first mixing step, followed by adding magnesium stearate lubricant in a later mixing step just prior to tabletting. Unexpectedly, the early introduction of magnesium stearate was found to interfere with the mixing of the other excipients. Yet, also unexpectedly, elimination of the sodium stearyl fumarate from the first mixing step resulted in blends with somewhat poor homogeneity and additional difficulties during tabletting. It was found that inclusion of both sodium stearyl fumarate in a first mixing step ("internal phase") and the inclusion of magnesium stearate in a third or final mixing step ("external phase") resulted in the most optimum tabletting process, with high homogeneity of the mix and minimal sticking during tabletting.

The table below includes further formulations that were investigated comprising 0% sodium stearyl fumarate introduced in the internal phase (and also 0% in the external phase) and different levels of magnesium stearate (0%, 0.5%, and 1% magnesium stearate) introduced in the external phase, prior to formation into tablets through direct compression.

|  | Number: | | |
|---|---|---|---|
|  | 15 | 16 | 17 |
| Venglustat malate | 13.5 | 13.4 | 13.4 |
| Pearlitol |  |  |  |
| Parteck | 69.4 | 69.1 | 68.7 |
| Avicel |  |  |  |
| Ac-Di-Sol |  |  |  |
| Kollidon CL | 8.0 | 8.0 | 7.9 |
| Poly. XL |  |  |  |
| Poly. XL-10 |  |  |  |
| Povidone |  |  |  |
| L-HPC | 5.0 | 5.0 | 5.0 |
| Aqualon T10 |  |  |  |
| Pruv |  |  |  |
| Hyqual |  | 0.5 | 1.0 |
| Silica | 1.0 | 1.0 | 1.0 |
| Apricot Flavor powder | 1.0 | 1.0 | 1.0 |
| Sucralose powder | 2.01 | 2.0 | 2.0 |

Formulations 15 to 17 were prepared according to the following steps: (a) approximately half to two thirds of the mannitol, the venglustat malate, the flavor (apricot), and the sweetener (sucralose) the silica are sieved with a 610 mm screen; (b) the sieved components are combined and blended in a tumble blender for 14 minutes at 10 rpm; (c) the remaining mannitol, the low-substituted hydroxypropyl cellulose, and the crospovidone are sieved, and are then added to the blend from step (b); (d) the resulting mixture is tumble blended for 14 minutes at 10 rpm; (e) the magnesium stearate (if any) is sieved with a 500 mm screen and is then added to the blend from step (d); (f) the mixture is blended in a turbula blender for 5 minutes at 34 rpm; and (g) the mixture is compressed to form 150 mg tablets (total weight).

Each of the Formulations 15 to 17 was found to exhibit acceptable flow behaviour, making them suitable for direct compression using a Fette 102i rotary tablet press (equipped with 7 mm punches ("7R7")), in order to form 15 mg (free base equivalent amount) tablets. However, Formulation 15 was found to be non-compliant in terms of homogeneity. During tableting of Formulation 16 (comprising 0.5% magnesium stearate), the ejection force in the tablet press reached its limit (indicative of sticking) and capping occurred at low compression force. Appreciably higher ejection forces during tableting were also required during tableting of Formulation 17 (comprising 1% magnesium stearate) in comparison to a formulation comprising 2.5% sodium stearyl fumarate introduced in the internal phase and 0.5% magnesium stearate introduced in the external phase. These results highlight the improved performance associated with the presence of sodium stearyl fumarate introduced in the internal phase, in combination with magnesium stearate introduced in the external phase.

The table below includes further formulations that were investigated comprising 2.5% sodium stearyl fumarate introduced in the internal phase and various levels of magnesium stearate (0%, 0.5%, and 1% magnesium stearate) additionally introduced in the external phase, prior to formation into tablets through direct compression.

|  | Number: | | |
|---|---|---|---|
|  | 18 | 19 | 20 |
| Venglustat malate | 13.4 | 13.4 | 13.3 |
| Pearlitol |  |  |  |
| Parteck | 68.1 | 67.7 | 67.4 |
| Avicel |  |  |  |
| Ac-Di-Sol |  |  |  |
| Kollidon CL | 8.0 | 7.9 | 8.0 |
| Poly. XL |  |  |  |
| Poly. XL-10 |  |  |  |
| Povidone |  |  |  |
| L-HPC | 5.0 | 5.0 | 5.0 |
| Aqualon T10 |  |  |  |
| Pruv | 2.5 | 2.5 | 2.5 |
| Hyqual |  | 0.5 | 1.0 |
| Silica | 1.0 | 1.0 | 1.0 |
| Apricot Flavor powder | 1.0 | 1.0 | 1.0 |
| Sweet Modulator* | 1.0 | 1.0 | 1.0 |

*mix containing potassium acesulfam E950 (46.7%) and natural flavor.

Formulations 18 to 20 were prepared according to the following steps: (a) approximately half to two thirds of the mannitol, the venglustat malate, the flavor (apricot), the sweetener, the silica, and the sodium stearyl fumarate are sieved with a 610-813 mm screen; (b) the sieved components are combined and blended in a tumble blender for 14 minutes at 10 rpm; (c) the remaining mannitol, the low-substituted hydroxypropyl cellulose, and the crospovidone are sieved, and are then added to the blend from step (b); (d) the resulting mixture is tumble blended for 14 minutes at 10 rpm; (e) the magnesium stearate is sieved with a 500 mm screen and is then added to the blend from step (d); (f) the mixture is tumble blended for 15 minutes at 10 rpm; and (g) the mixture is compressed to form 150 mg tablets (total weight).

Each of the Formulations 18 to 20 was compressed using a Stylcam compaction simulator (equipped with 7 mm punches ("7R7")) in order to form 15 mg (free base equivalent amount) tablets. For Formulation 18, the absence of magnesium stearate introduced during the external phase resulted in much higher ejection forces being required during tableting, whilst the presence of 0.5% to 1% magnesium stearate introduced in the external phase allows for a substantial decrease in the ejection forces, as shown in appended FIG. 1. Formulations 19 and 20 also exhibited substantially lower mass variability after tableting in comparison to Formulation 18. FIG. 1 also shows that very similar results are achieved for Formulations 19 and 20 (comprising 0.5% and 1% magnesium stearate introduced in the external phase, respectively), indicating that the full extent of the benefits associated with the presence of magnesium stearate may be derived at concentrations of less than 1%.

The table below includes a yet further formulation that was investigated comprising 1.5% sodium stearyl fumarate introduced in the internal phase and 0.5% magnesium stearate additionally introduced in the external phase, prior to formation into a tablet through direct compression.

|  | Number: 21 |
|---|---|
| Venglustat malate | 13.6 |
| Pearlitol |  |
| Parteck | 67.4 |
| Avicel |  |
| Ac-Di-Sol |  |
| Kollidon CL | 8.0 |
| Poly. XL |  |
| Poly. XL-10 |  |
| Povidone |  |
| L-HPC | 5.0 |
| Aqualon T10 |  |
| Pruv | 1.5 |
| Hyqual | 0.5 |
| Silica | 1.0 |
| Apricot Flavor powder | 1.0 |
| Sucralose powder | 2.0 |

Formulation 21 was prepared according to the following steps: (a) approximately half to two thirds of the mannitol, the venglustat malate, the flavor (apricot), the sweetener, the silica, and the sodium stearyl fumarate are sieved with a 610-813 mm screen; (b) the sieved components are combined and blended in a tumble blender for 14 minutes at 10 rpm; (c) the remaining mannitol, the low-substituted hydroxypropyl cellulose, and the crospovidone are sieved, and are then added to the blend from step (b); (d) the resulting mixture is tumble blended for 14 minutes at 10 rpm; (e) the magnesium stearate is sieved with a 500 mm screen and is then added to the blend from step (d); (f) the mixture is tumble blended for 5 minutes at 34 rpm; and (g) the mixture is compressed to form 20 mg tablets (total weight).

Formulation 21 was compressed using a Fette 102i rotary press (equipped with 3.2 mm punches ("3.2R4")) in order to form 2 mg (free base equivalent amount) tablets, which were found to have acceptable ejection forces during tableting. However, Formulation 21 was nevertheless found to require fractionally higher ejection forces during tableting than a comparable formulation comprising 2.5% sodium stearyl fumarate (as opposed to 1.5%) introduced in the internal phase and the same amount of magnesium stearate (0.5%) introduced in the external phase (based on a comparison with normalized values for higher dose tablets). Thus, the use of a higher sodium stearyl fumarate content (2.5%) introduced in the internal phase was considered to be optimal in reducing the amount of magnesium stearate required to achieve acceptable ejection forces during tableting, so as to avoid sticking issues, whilst also avoiding any unnecessary increases in tablet disintegration times which have been observed upon increasing magnesium stearate lubrication in the external phase.

Accordingly, the optimal tablet compositions were found to be:

| Tablet Formulation A-1 | |
|---|---|
| Ingredient | 15 mg (free base equivalent amount) Tablet (Wt. %) |
| Venglustat Malate | 13.4% (20.16 mg) |
| Mannitol | Q.S. |
| Crospovidone (Type A) | 8.0% |
| Low-sub HPC | 5.0% |
| Colloidal silica | 1.0% |
| Sodium stearyl fumarate | 2.5% |
| Magnesium stearate | 0.5% |
| Flavor | 1.0% |
| Sweetener | 2.0% |
| Tablet Weight | 150 mg |

| Tablet Formulation A-2 | |
|---|---|
| Ingredient | 15 mg (free base equivalent amount) Tablet (Wt. %) |
| Venglustat Malate | 13.4% (20.16 mg) |
| Mannitol | Q.S. |
| Crospovidone (Type A) | 8.0% |
| Low-sub HPC | 5.0% |
| Colloidal silica | 1.0% |
| Sodium stearyl fumarate | 2.5% |
| Magnesium stearate | 0.5% |
| Flavor | 1.0% |
| Sweetener | 1.0% |
| Tablet Weight | 150 mg |

| Tablet Formulation A-3 | |
|---|---|
| Ingredient | 15 mg (free base equivalent amount) Tablet (Wt. %) |
| Venglustat Malate | 13.4% (20.16 mg) |
| Mannitol | Q.S. |

-continued

| Tablet Formulation A-3 | |
|---|---|
| Ingredient | 15 mg (free base equivalent amount) Tablet (Wt. %) |
| Crospovidone (Type A) | 8.0% |
| Low-sub HPC | 5.0% |
| Colloidal silica | 1.0% |
| Sodiumstearyl fumarate | 2.5% |
| Magnesium stearate | 0.5% |
| Flavor | 1.0% |
| Sweetener | 0% |
| Tablet Weight | 150 mg |

Tablet Formulation A (A-1, A-2 and A-3) is prepared according to the following steps: (a) approximately half to two thirds of the mannitol, the venglustat malate, the flavor (apricot), the sweetener (sucralose, if any) the silica, and the sodium stearyl fumarate are sieved with a 710-1140 m screen; (b) the sieved components are combined and blended in a tumble blender; (c) the remaining mannitol, the low-substituted hydroxypropyl cellulose, and the crospovidone are sieved, and are then added to the blend from step (b); (d) the resulting mixture is tumble blended for 20 minutes at 7 rpm; (e) the magnesium stearate is sieved with a 500 m screen and is then added to the blend from step (d); (f) the mixture is tumble blended for 3 minutes at 7 rpm; and (g) the mixture is compressed to form 150 mg tablets.

Appropriate amounts of formulation (homothetic in composition) were used as required for the formation of 4 mg, 6 mg, and 15 mg tablets (free base equivalent amount), corresponding to total tablet weights of 40 mg, 60 mg, and 150 mg, respectively. 4 mg tablets were round with a 4.5 mm diameter. 6 mg tablets were oblong with a 3.8×7 mm dimensions. 15 mg tablets were round with a 7 mm diameter. Importantly, as all tablets have dimensions smaller than 8 mm, the tablets will be effective for patients with swallowing difficulties. Because patients with swallowing difficulty may prefer to chew the tablets, the tablets are each formulated for effective chewability, including taste, mouthfeel, and hardness. It is found that each of the 4, 6, and 15 mg tablets have a chewing difficulty index of less than 0.6 Nm, which is considered satisfactory for this patient population. The 15 mg tablets according to Tablet Formula A have a chewing difficulty index of less than 0.5 Nm, while the 4 and 6 mg tablets have a chewing difficulty index of less than 0.2 Nm.

Dissolution testing was performed as described in the preceding section. The following results were obtained for the tablet prepared according to Tablet Formulation A-1 (mean, n=12, % dissolved):

| Aqueous HCl (pH 1.2) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| Tab. A-1 | 99.3 | 98.3 | 98.2 | 98.2 | 98.1 | 98.1 | 98.1 | 98.2 | 98.2 | 98.3 | 98.4 | 98.2 |

| Aqueous Acetate (pH 4.5) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| Tab. A-1 | 97.0 | 96.0 | 96.0 | 96.0 | 96.0 | 96.0 | 96.0 | 96.0 | 96.0 | 95.9 | 95.9 | 95.9 |

| Aqueous Phosphate (pH 6.8) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| Tab. A-1 | 91.1 | 94.1 | 94.6 | 94.7 | 94.8 | 94.7 | 95.0 | 95.1 | 95.0 | 95.0 | 94.9 | 95.0 |

The results show that tablets according to Tablet Formulation A-1 undergo rapid dissolution over a broad pH range. The same properties are to be expected for Tablet Formulations A-2 and A-3. A dissolution study was performed on Tablet Formulation A-3, and the following results were obtained:

| Aqueous HCl (pH 1.2) (n = 12) | | | | | | | | | |
|---|---|---|---|---|---|---|---|---|---|
| Time (min): | 5 | 10 | 15 | 20 | 25 | 30 | 35 | 40 | 45 |
| Tab. A-3 | 96.0 | 96.2 | 96.3 | 96.2 | 96.2 | 96.1 | 96.6 | 96.7 | 96.5 |

| Aqueous Acetate (pH 4.5) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| Tab. A-3 | 96.7 | 97.7 | 98.2 | 98.2 | 98.2 | 98.2 | 98.3 | 98.4 | 98.3 | 98.2 | 98.4 | 98.3 |

-continued

| Aqueous Phosphate (pH 6.8) | | | | | | | | | | | | |
|---|---|---|---|---|---|---|---|---|---|---|---|---|
| Time (min): | 5 | 10 | 15 | 20 | 25 | 30 | 35 | 40 | 45 | 50 | 55 | 60 |
| Tab. A-3 | 94.6 | 96.7 | 97.6 | 97.8 | 97.9 | 97.8 | 97.8 | 97.8 | 97.8 | 97.8 | 97.8 | 97.8 |

Palatability is an important concern for patients who chew their tablets due to swallowing difficulties. Venglustat malate is a bitter-tasting substance, so it is essential to mask this taste to ensure patient compliance.

Tablets according to Tablet Formulation A-1 containing 2% of sucralose as sweetener and 1% of apricot flavor were initially developed. A palatability study was then conducted with the highest strength (15 mg) on 12 healthy adult volunteers. They tested the organoleptic characteristics of five different chewable tablet formulations of venglustat with different percentages of apricot flavor (from 0 to 1%) and sucralose as sweetener (from 1 to 2%) compared to a control formulation without apricot flavor or sweetener. The results demonstrated a positive effect for the flavor, with a much more limited impact from the sucralose sweetener (i.e., comparable taste from 1 to 2% sweetener). Optimal results appeared to be obtained from including 1% apricot flavor and 1% sucralose (Tablet Formulation A-2).

An important consideration in formulation development is the chemical stability of the active ingredient. UPLC analysis is performed using reverse phase gradient elution with a C18 Acquity CSH Waters stationary phase and water/acetonitrile (0.1% v/v TFA) mobile phase at 0.4 mL/min. Satisfactory results require that the major venglustat degradation product, the N-oxide (compound of Formula A) is present at less than or equal to 0.50% by UPLC, that other unspecified degradation products amount to no more than 0.20% individually, and that total degradation products amount to no more than 1.5% collectively (including N-oxide). Analysis of finished 15 mg tablets indicates that the N-oxide is undetectable, and that no unspecified degradation product is present at more than 0.10%.

Stability studies were then conducted on tablets at 4 mg, 6 mg, and 15 mg dosages, with formulas according to Tablet Formula A-1 having 1 wt. % apricot flavor and 2 wt. % sucralose. Stability was assessed over up to 18 months at 30° C. and 65% relative humidity, and up to 6 months at 40° C. and 75% relative humidity. Satisfactory results were obtained on all critical parameters, including UPLC assay (including degradation products), dissolution profile, water content, disintegration, resistance to crushing/breaking, and microbial examination.

However, it is surprisingly found that replacement of the sucralose with additional mannitol diluent (mannitol being a slightly sweet sugar alcohol) provides sufficient palatability for chewing. Thus, by comparison of the formulas evaluated during the palatability study described above, it is anticipated that the positive effect resulting from the apricot flavor should be sufficient to compensate for the absence of sucralose in the formulation.

The present disclosure also provides compositions, processes for their manufacture, and methods of treatment according to the following clauses:

1. An oral pharmaceutical composition, comprising venglustat:

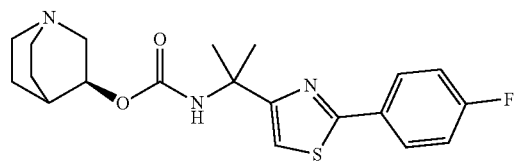 [SMILES: CC(C)(NC(=O)O[C@@H]1CN2CCC1CC2)c1csc(-c2ccc(F)cc2)n1]

in free base or pharmaceutically acceptable salt form (e.g., in malate salt form).
2. The composition of clause 1, wherein the composition comprises the venglustat in pharmaceutically acceptable salt form, e.g., acid addition salt form.
3. The composition of clause 2, wherein the acid addition salt form is selected from hydrochloride, hydroxysuccinate, and malate.
4. The composition of clause 2, wherein the acid addition salt form is malate salt form.
5. The composition of any one of clauses 1-4, wherein the composition is a finished dosage form, e.g., a capsule or a tablet, optionally wherein said finished dosage form comprises from about 2 to about 30 mg of venglustat (measured as the equivalent amount of free base), e.g. from about 4 mg to about 20 mg, or from about 8 mg to about 12 mg, or about 4 mg, or about 6 mg, or about 8 mg, or about 12 mg, or about 15 mg of venglustat (measured as the equivalent amount of free base).
6. The composition of clause 5, wherein the tablet is selected from a chewable tablet, orally-disintegrating tablet, dispersible tablet, or a classic tablet or caplet.
7. The composition of clause 6, wherein the tablet comprises from about 4 mg to about 20 mg of venglustat (measured as the equivalent amount of free base).
8. The composition of any one of clauses 1-7, wherein the composition further comprises one or more pharmaceutically acceptable excipients.
9. The composition of clause 8, wherein the one or more pharmaceutically acceptable excipients comprises one or more of (a) diluent/filler, (b) binder, (c) disintegrant, (d) lubricant, (e) a glidant, (f) sweetener or (g) flavor, and (h) dye or colorant.
10. The composition of clause 9, wherein the one or more pharmaceutically acceptable excipients comprises one or more of (a) diluent/filler selected from cellulose or microcrystalline cellulose, mannitol, or lactose, (b) binder selected from povidone, methylcellulose, ethylcellulose, hydroxypropyl cellulose, low-substituted hydroxypropyl cellulose, or hydroxypropyl methylcellulose, (c) disintegrant selected from crospovidone, sodium starch glycolate, or croscarmellose sodium, (d) lubricant selected from magnesium stearate, sodium stearyl fumarate, (e) a glidant selected from silica or talc, (f) sweetener selected from sucralose, acesulfame potassium, aspartame, saccharine, neotame, advantame, or (g) apricot flavor, and (h) dye or colorant.
11. The composition of any one of clauses 1 to 8, wherein the composition comprises or consists of (a) venglustat, (b) the diluents/fillers mannitol and/or cellulose, (c) the lubricants magnesium stearate and/or sodium stearyl fumarate, (d) the disintegrants croscarmellose sodium and/or crospovidone, (e) the binders povidone, ethylcellulose, and/or hydroxypropyl cellulose, (f) the glidant silica, and (g) flavor, sweetener and/or color.

12. The composition of clause 11, wherein the composition is a capsule, comprising or consisting of (a) venglustat, (b) the diluents/filler cellulose, (c) the lubricant magnesium stearate, (d) the disintegrant croscarmellose sodium, (e) the glidant silica, (f) flavor, sweetener and/or color, and (g) a capsule shell.

13. The composition of clause 11, wherein the composition is a tablet, comprising or consisting of (a) venglustat, (b) the diluents/fillers mannitol and/or cellulose, (c) the lubricants magnesium stearate and/or sodium stearyl fumarate, (d) the disintegrants croscarmellose sodium and/or crospovidone, (e) the binders povidone, ethylcellulose, and/or hydroxypropyl cellulose, (f) the glidant silica, and (g) flavor, sweetener and/or color.

14. The composition of any one of clauses 10-13, wherein the cellulose is microcrystalline cellulose.

15. The composition of any one of clauses 10-14, wherein the silica is colloidal and/or anhydrous silica.

16. The composition of clause 11, wherein the composition is a tablet, comprising or consisting of (a) venglustat, (b) the diluent/filler mannitol, (c) the lubricants magnesium stearate and sodium stearyl fumarate, (d) the disintegrant crospovidone, (e) the binder hydroxypropyl cellulose, (f) the glidant anhydrous colloidal silica, and (g) flavor, sweetener and/or color.

17. The composition of any one of clauses 10-16, wherein the hydroxypropyl cellulose is low-substituted hydroxypropyl cellulose.

18. The composition of any one of clauses 1 to 17, wherein the composition comprises (a) from 3% to 20% by weight of venglustat, measured as the free base equivalent; (b) from 60-90% by weight of diluent(s)/filler(s); (c) from 0.5-6% by weight of lubricant(s); (d) from 2-15% by weight of disintegrant(s); (e) from 1-12% by weight of binder(s); (f) from 0-5% by weight of glidant(s); and (g) from 0-2% by weight of flavor(s), 0-2% by weight of sweetener(s) and/or 0-2% by weight of color(s).

19. The composition of any one of clauses 1 to 18, wherein the composition comprises (a) from 3% to 20% by weight of venglustat, measured as the free base equivalent; (b) from 60 to 90% by weight of diluent(s)/filler(s); (c) from 0.5-6% by weight of lubricant(s); (d) from 2-15% by weight of disintegrant(s); (e) from 1-12% by weight of binder(s); (f) from 0-5% by weight of glidant(s); and (g) from 0-2% by weight of flavor(s), 0-2% by weight of sweetener(s) and/or 0-2% by weight of color(s).

20. The composition of clause 19, wherein the composition comprises (a) 13-20% by weight of venglustat, measured as the free base equivalent, (b) from 60-70% by weight of diluent(s)/filler(s); (c) from 2-4% by weight of lubricant(s); (d) from 6-10% by weight of disintegrant(s); (e) from 2-6% by weight of binder(s); (f) from 0.5-1.5% by weight of glidant(s); and from 0-2% by weight of flavor(s), 0-2% by weight of sweetener(s) and/or 0-2% by weight of color(s).

21. The composition of any one of clauses 1 to 19, wherein the composition comprises or consists of (a) from 7.5 to 12.5% by weight of venglustat, measured as the free base equivalent; (b) from 60 to 90% by weight of mannitol; (c) from 0.5-6% by weight of sodium stearyl fumarate and magnesium stearate; (d) from 2-15% by weight of crospovidone; (e) from 1-12% by weight of hydroxypropyl cellulose; (f) from 0-5% by weight of anhydrous colloidal silica; and (g) from 0-2% by weight of flavor(s), 0-2% by weight of sweetener(s) and/or 0-2% by weight of color(s).

22. The composition of clause 21, wherein the composition comprises or consists of (a) from 7.5 to 12.5% by weight of venglustat, measured as the free base equivalent; (b) from 60 to 70% by weight of mannitol; (c) from 2-4% by weight of sodium stearyl fumarate and magnesium stearate; (d) from 6-10% by weight of crospovidone; (e) from 2-6% by weight of hydroxypropyl cellulose; (f) from 0.5-1.5% by weight of anhydrous colloidal silica; and (g) from 0-2% by weight of flavor(s), 0-2% by weight of sweetener(s) and/or 0-2% by weight of color(s).

23. The composition of any one of clauses 1 to 5, or any of clauses 8 to 12, 14, 15 and 17 to 22, wherein the composition is a hard-shelled capsule, e.g., wherein said capsule contains a mixture of venglustat and the any one or more pharmaceutically acceptable excipients, and said venglustat and other diluents/carriers are comprised as granules or pellets, or as a powder, said granules, pellets or powder being contained within the shell of the capsule.

24. The composition of any one of clauses 1 to 11 and 13 to 22, wherein the composition is a tablet formed by direct compression of a mixture of venglustat and the any one or more pharmaceutically acceptable excipients.

25. The composition of any one of clauses 1 to 24, wherein the venglustat is venglustat malate.

26. The composition of clause 25, wherein the composition comprises or consists of (a) venglustat malate in an amount from about 9-11% by weight of venglustat free base equivalent; (b) from 60 to 70% by weight of mannitol; (c) from 2-6% by weight of sodium stearyl fumarate, and 0.1-3% magnesium stearate; (d) from 5-15% by weight of crospovidone; (e) from 2-8% by weight of hydroxypropyl cellulose; (f) from 0.1-3% by weight of anhydrous colloidal silica; (g) from 0.5-3% by weight of flavor; and (h) from 0-2% by weight of sweetener.

27. The composition of clause 26, wherein the composition comprises or consists of (a) venglustat malate in an amount from about 9-11% by weight of venglustat free base equivalent; (b) from 65 to 70% by weight of mannitol; (c) from 2-3% by weight of sodium stearyl fumarate, and 0.1-1% magnesium stearate; (d) from 7-9% by weight of crospovidone; (e) from 4-6% by weight of low-substituted hydroxypropyl cellulose; (f) from 0.5-1.5% by weight of anhydrous colloidal silica; (g) from 0.5-3% by weight of flavor; and (h) from 0-2% by weight of sweetener.

28. The composition of any one of clauses 1 to 27, wherein the composition is formulated for immediate-release.

29. The composition of any one of clauses 1 to 28, wherein the composition provides at least 80% dissolution within 15 minutes (e.g., using FDA and/or EMEA immediate-release solid oral dosage form testing guidelines), such as in pH 1.2 (HCl), pH 4.5 (acetate buffer) or pH 6.8 (phosphate buffer) dissolution medium, for example 85-100% dissolution.

30. The composition of clause 29, wherein the composition provides at 85-100% dissolution within 15 minutes.
31. The composition of any one of clauses 1 to 11, 13 to 22 and 24 to 30, wherein the composition is a chewable tablet.
32. The composition of clause 31, wherein the chewable tablet has a chewing difficulty index selected from less than 0.6 Nm, or less than 0.5 Nm, or less than 0.4 Nm, or less than 0.2 Nm.
33. A process for the manufacture of the composition according to any one of clauses 1 to 32, wherein the process comprises the steps of:
    (a) sieving each ingredient;
    (b) combining venglustat, in free base or pharmaceutically acceptable salt form, with a diluent/filler, and optionally with a glidant, a lubricant, any colors or flavors, or any other excipients, or a combination thereof;
    (c) blending and/or milling and/or granulating the resulting the mixture;
    (d) optionally filtering the resulting mixture;
    (e) adding at least one other diluent or carrier to the mixture, such as additional diluent/filler, a disintegrant, a binder, or any other excipient, or a combination thereof;
    (f) blending and/or milling and/or granulating the resulting mixture;
    (g) optionally filtering the resulting mixture;
    (h) adding any additional excipients, e.g., a lubricant;
    (i) blending and/or milling the resulting mixture;
    (j) granulating the resulting mixture;
    (k) optionally filtering the resulting mixture;
    (l) encapsulating the resulting material; or compressing the resulting material to form a tablet;
    (m) optionally applying one or more coatings to the capsule, tablet or other dosage form; and
    (n) optionally packaging the resulting finished dosage form.
34. The process according to clause 33, wherein the venglustat is venglustat malate, and the diluent/filler is mannitol, and the disintegrant is crospovidone, and the binder is hydroxypropyl cellulose, and the lubricant is sodium stearyl fumarate and magnesium stearate, and the glidant is silica.
35. A method for the treatment or prevention of a disease or disorder susceptible to treatment by GCS inhibition, comprising administering to a patient in need thereof the composition according to any one of clauses 1 to 32.

We claim:
1. A process for the manufacture of an oral pharmaceutical composition comprising venglustat, (S)-quinuclidin-3-yl(2-(2-(4-fluorophenyl)thiazol-4-yl)propan-2-yl)carbamate:

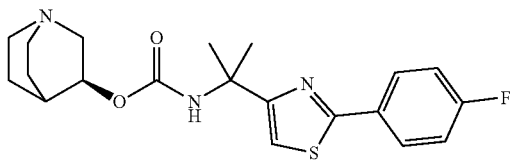 [SMILES: CC(C)(NC(=O)O[C@@H]1CN2CCC1CC2)c1csc(-c2ccc(F)cc2)n1]

in free base or pharmaceutically acceptable salt form, wherein the composition is a finished dosage form which is a tablet, and wherein the process comprises the steps of:
    (a) sieving each ingredient;
    (b) combining venglustat, in free base or pharmaceutically acceptable salt form, with a diluent/filler, and with sodium stearyl fumarate as a first lubricant, and optionally with a glidant, any colors or flavors, or any other excipients, or a combination thereof;
    (c) blending and/or milling and/or granulating the resulting the mixture;
    (d) optionally screening the resulting mixture;
    (e) adding at least one other diluent or carrier to the mixture;
    (f) blending and/or milling and/or granulating the resulting mixture;
    (g) optionally screening the resulting mixture;
    (h) adding magnesium stearate as a second lubricant and any additional excipients;
    (i) blending and/or milling the resulting mixture;
    (j) optionally granulating the resulting mixture;
    (k) optionally screening the resulting mixture;
    (l) compressing the resulting material to form a tablet;
    (m) optionally applying one or more coatings to the tablet; and
    (n) optionally packaging the resulting finished dosage form.
2. The process according to claim 1, wherein the venglustat is venglustat malate.
3. The process according to claim 1, wherein steps (i), (j), and/or (k) are repeated for additional excipients added in step (h) before proceeding to steps (l), (m), or (n).
4. The process according to claim 1, wherein the magnesium stearate is added as the final excipient added before final mixing and compression to form the tablet.
5. The process according to claim 1, wherein the diluent/filler is mannitol, and the disintegrant is crospovidone, and the binder is hydroxypropyl cellulose, and the glidant is silica.
6. The process according to claim 1, wherein the process comprises the following steps:
    (a) sieving each of a first portion of mannitol, silica, venglustat malate, flavor, and sodium stearyl fumarate, and optionally sucralose;
    (b) combining the venglustat malate with the sieved mannitol, silica, flavor, and sodium stearyl fumarate, and optionally sucralose, optionally wherein each ingredient is sieved sequentially into a common container to combine the ingredients;
    (c) blending and/or milling and/or granulating the resulting mixture;
    (e) sieving a second portion of mannitol, low-substituted hydroxypropyl cellulose, and crospovidone, and adding these sieved ingredients to the mixture from step (c);
    (f) blending and/or milling and/or granulating the resulting mixture;
    (h) sieving magnesium stearate and adding it to the mixture from step (f);
    (i-j) blending and/or milling and/or granulating the resulting mixture;
    (l) compressing the resulting material to form a tablet; and
    (n) optionally packaging the resulting finished dosage form.
7. The process according to claim 6, wherein sodium stearyl fumarate is combined in step (b) in an amount to provide 2-3% by weight of sodium stearyl fumarate in the tablet.
8. The process according to claim 6, wherein magnesium stearate is added in step (h) in an amount to provide from 0.1-1% by weight of magnesium stearate in the tablet.

9. A process for the manufacture of an oral pharmaceutical composition comprising venglustat, (S)-quinuclidin-3-yl(2-(2-(4-fluorophenyl)thiazol-4-yl)propan-2-yl)carbamate:

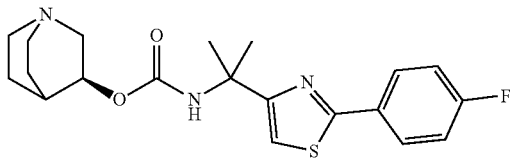

in free base or pharmaceutically acceptable salt form, wherein the composition is a finished dosage form which is a capsule, and wherein the process comprises the steps of:
(a) sieving each ingredient;
(b) combining venglustat, in free base or pharmaceutically acceptable salt form, with a diluent/filler, and optionally with a glidant, any colors or flavors, or any other excipients, or a combination thereof;
(c) blending and/or milling and/or granulating the resulting the mixture;
(d) optionally screening the resulting mixture;
(e) adding at least one other diluent or carrier to the mixture and adding a first portion of magnesium stearate as a lubricant to the mixture;
(f) blending and/or milling and/or granulating the resulting mixture;
(g) optionally screening the resulting mixture;
(h) adding the remaining portion of magnesium stearate as a lubricant and any additional excipients;
(i) blending and/or milling the resulting mixture;
optionally granulating the resulting mixture;
(k) optionally screening the resulting mixture;
(l) filling the resulting material into hard capsules; and
(m) optionally applying one or more coatings to the capsule; and
(n) optionally packaging the resulting finished dosage form;
wherein steps (i), (j), and/or (k) are repeated for additional excipients added in step (h) before proceeding to steps (l), (m), or (n).

10. The process according to claim 9, wherein the venglustat is venglustat malate.

11. A process for the manufacture of an oral pharmaceutical composition comprising venglustat, (S)-quinuclidin-3-yl(2-(2-(4-fluorophenyl)thiazol-4-yl)propan-2-yl)carbamate:

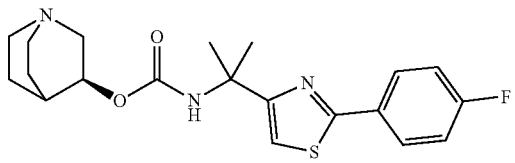 [SMILES: CC(C)(NC(=O)O[C@@H]1CN2CCC1CC2)c1csc(-c2ccc(F)cc2)n1]

in malate salt form, wherein the composition is a finished dosage form which is a capsule, wherein the process comprises the following steps:
(a) sieving one or more ingredients to be used in step (b);
(b) combining venglustat malate with a first portion of microcrystalline cellulose, and croscarmellose sodium, optionally sucralose and optionally flavor, optionally wherein these ingredients are not previously sieved;
(c) blending and/or milling and/or granulating the resulting mixture;
(d) optionally sieving the resulting mixture;
(e) adding a second portion of microcrystalline cellulose, silica, and a first portion of magnesium stearate to the mixture from step (c), optionally wherein these added ingredients are previously sieved from step (a);
(f) blending and/or milling and/or granulating the resulting mixture;
(h) sieving the remaining portion of magnesium stearate and/or adding it to the mixture from step (f);
(i-j) blending and/or milling and/or granulating the resulting mixture;
(l) filling the resulting material into hard capsules; and
(n) optionally packaging the resulting finished dosage form.

12. The process according to claim 11, wherein the first portion of magnesium stearate comprises 15-50% by weight, or 20-30% by weight of the total magnesium stearate lubricant added, and wherein the remaining portion of magnesium stearate comprises 50-85% by weight, or 70-80% by weight, of the total magnesium stearate lubricant added.

\* \* \* \* \*